US008337462B2

(12) United States Patent
Shirley et al.

(10) Patent No.: US 8,337,462 B2
(45) Date of Patent: Dec. 25, 2012

(54) MINIMALLY INVASIVE MEDICAL DEVICE AND METHOD FOR DELIVERY OF THERAPEUTIC OR DIAGNOSTIC AGENTS INTO A VESSEL WALL

(75) Inventors: Brad Shirley, Bloomington, IN (US); Grant T. Hoffman, Bloomington, IN (US); Michael W. Hardert, Bloomington, IN (US); Jeffry S. Meisheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/209,145

(22) Filed: Aug. 12, 2011

(65) Prior Publication Data
US 2011/0295228 A1    Dec. 1, 2011

Related U.S. Application Data

(62) Division of application No. 11/827,219, filed on Jul. 10, 2007, now Pat. No. 8,007,470.

(51) Int. Cl.
*A61M 5/178* (2006.01)
(52) U.S. Cl. .................... 604/164.01; 604/506; 604/264
(58) Field of Classification Search .................. 623/1.42, 623/1.23, 1.14
See application file for complete search history.

(56) References Cited

U.S. PATENT DOCUMENTS

| 2,792,003 A | 5/1957 | Cantor |
| 4,739,762 A | 4/1988 | Palmaz |
| 4,936,823 A | 6/1990 | Colvin et al. |
| 5,133,732 A | 7/1992 | Wiktor |
| 5,147,379 A | 9/1992 | Sabbaghian et al. |
| 5,176,996 A | 1/1993 | Hogan et al. |
| 5,256,775 A | 10/1993 | Froehler |
| 5,264,564 A | 11/1993 | Matteucci |
| 5,292,331 A | 3/1994 | Boneau |
| 5,421,955 A | 6/1995 | Lau et al. |

(Continued)

FOREIGN PATENT DOCUMENTS
WO    WO 98/53761    5/1998

OTHER PUBLICATIONS

Sambrook, Fritsch and Maniatis, Molecular Cloning a Laboratory Manual, 2nd Ed., ed. Cold Spring Harbor Laboratory Press, Chapters 16 and 17 (1989).

(Continued)

*Primary Examiner* — David H Willse
*Assistant Examiner* — Tiffany Shipmon
(74) *Attorney, Agent, or Firm* — Brinks Hofer Gilson & Lione

(57) ABSTRACT

The invention relates to minimally invasive device for delivering therapeutic or diagnostic agents into a vessel wall. The device includes an introducer tube, a tubular member having a proximal end, a distal end, and a first lumen extending therebetween, the tubular member being slidably disposed within the introducer tube; a plurality of hollow delivery struts, each delivery strut adapted to pierce through inner most layers of the vessel wall and each comprising at least one exit port and at least one stopper to prevent the delivery strut from piercing through the outer most layers of the vessel wall. The delivery struts are disposed on the distal end of the tubular member and are in fluid communication with the first lumen. The invention also relates to methods of delivering the device of this invention and methods of treating conditions or diseases of body lumens.

19 Claims, 15 Drawing Sheets

U.S. PATENT DOCUMENTS

| | | | |
|---|---|---|---|
| 5,713,853 | A | 2/1998 | Clark et al. |
| 5,834,449 | A | 11/1998 | Thompson et al. |
| 6,090,127 | A | 7/2000 | Globerman |
| 6,152,931 | A | 11/2000 | Nadal et al. |
| 6,217,554 | B1 | 4/2001 | Green |
| 6,273,901 | B1 | 8/2001 | Whitcher et al. |
| 6,689,099 | B2 | 2/2004 | Mirzaee |
| 6,716,208 | B2 | 4/2004 | Humes |
| 6,905,480 | B2 | 6/2005 | McGuckin, Jr. et al. |
| 2003/0088211 | A1 | 5/2003 | Anderson et al. |
| 2004/0093064 | A1 | 5/2004 | Bosma |
| 2004/0236346 | A1 | 11/2004 | Parker |
| 2005/0266043 | A1 | 12/2005 | Tseng et al. |
| 2006/0004441 | A1 | 1/2006 | Tiisrna et al. |
| 2006/0069405 | A1 | 3/2006 | Schaeffer et al. |

OTHER PUBLICATIONS

Kim W. and Kang K, "Recent developments of cathepsin inhibitors and their selectivity," *Expert Opin. Ther. Patents*, 12(3):419-432 (2002).

Camenzind E and De Scheerder IK, "Local Drug Delivery for Coronary Artery Disease," *Martin Dunitz, an imprint of the Taylor & Francis Group pic*, Chapter 19: "Overview of potential drugs to inhibit in- stent restenosis," pp. 171-172 (2005).

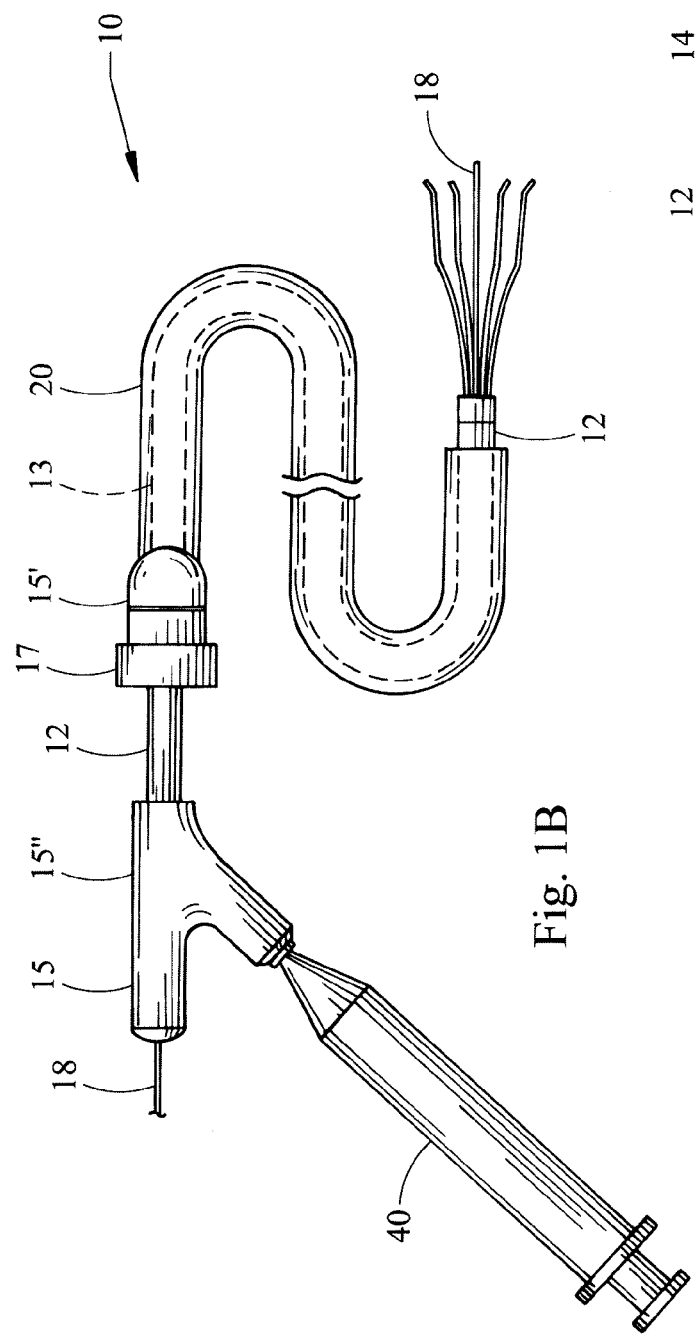
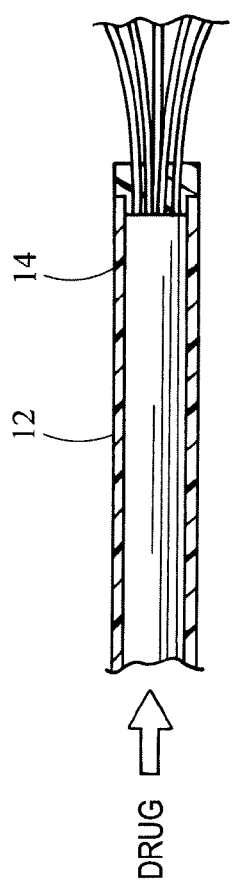
Fig. 1B
Fig. 1C

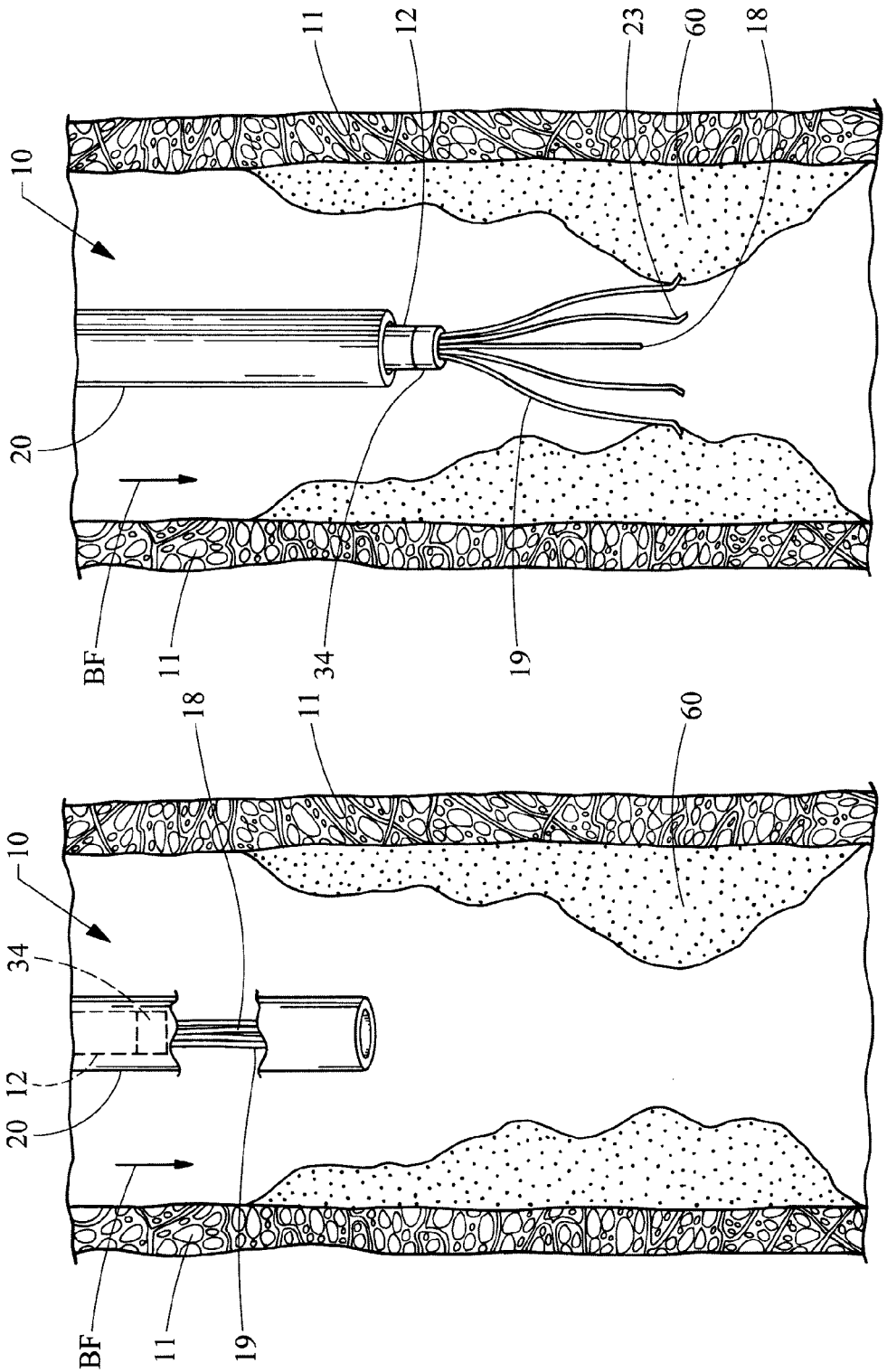

MINIMALLY INVASIVE MEDICAL DEVICE AND METHOD FOR DELIVERY OF THERAPEUTIC OR DIAGNOSTIC AGENTS INTO A VESSEL WALL

RELATED APPLICATIONS

The present patent document is a divisional application of U.S. patent application Ser. No. 11/827,219, filed Jul. 10, 2007, which is hereby incorporated by reference in its entirety.

BACKGROUND

1. Technical Field

The present invention relates to minimally invasive devices, methods for delivering therapeutic or diagnostic agents into a vessel wall of a patient, and methods of treating various conditions or diseases of the vessel wall.

2. Background Information

A number of techniques have been developed for injecting therapeutic agents, such as drugs and bioactive agents, near or into the walls of vessels and surrounding tissues.

For example, U.S. Pat. No. 6,689,099 to Mirzaee described a catheter for injecting medication to a specific point within a patient, where the catheter includes a mechanism for angularly pushing an injection port outwardly away from the body of the catheter into an artery wall so that medication can be injected directly into the artery wall.

U.S. Pat. No. 6,217,554 to Green described an apparatus and a method for delivering a therapeutic or diagnostic agent into extravascular tissue surrounding a body passageway, which includes a catheter having a sheath, a tubular member, and a plurality of hollow needles on a distal end of the tubular member. The tubular member of Green is selectively movable between delivery position, wherein the plurality of hollow needles are retracted within the sheath, and an extended position, wherein the plurality of hollow needles extend beyond a distal endface of the sheath to pierce and penetrate extravascular tissue.

There still exists a need for improved minimally invasive devices capable of delivering therapeutic or diagnostic agents into the vessel wall at multiple treatment locations without going through the outer vessel wall and into the extravascular tissue.

SUMMARY

The present invention generally relates to minimally invasive devices for delivering therapeutic or diagnostic agents into a vessel wall of a patient and methods for providing such minimally invasive devices, methods of delivering therapeutic or diagnostic agents to the vessel wall, and methods of treating various conditions or diseases of the vessel wall.

In one embodiment, the present invention includes a minimally invasive device for delivering therapeutic or diagnostic agents into a vessel wall, including an introducer tube; a tubular member having a proximal end, a distal end, and a first lumen extending therebetween, the tubular member being slidably disposed within the introducer tube; and a plurality of hollow delivery struts, each delivery strut adapted to pierce through inner most layers of the vessel wall. Each delivery strut includes at least one exit port and at least one stopper to prevent the delivery strut from piercing through the outer most layers of the vessel wall. The delivery struts are disposed on the distal end of the tubular member and are in fluid communication with the first lumen. The device may also include an endcap affixed to the distal portion of the tubular member, the plurality of hollow delivery struts being affixed to a distal face of the endcap. The hollow delivery struts may be arranged in a pattern on the distal face of the endcap. The exit port may be an opening at a tip of the delivery strut. Each delivery strut may include multiple exit ports. The exit ports may be arranged around the circumference of the delivery strut. The stopper may be disposed about the outer surface of the hollow delivery struts. The stopper may be disposed by welding, use of adhesive, crimping, or by any mechanical or chemical fixation. Alternatively, the stopper may be a protrusion from the delivery strut. The device may also include an extension at the distal end of at least one of the delivery struts. The exit port may be located on the extension. A plurality of exit ports may be located on the extension. The extension may be in fluid communication with the delivery strut. The extension may be the stopper. The delivery struts may also include at least one fixation element. The fixation element may be a barb or a hook. The device may also include a wire guide. The tubular member may also include a second lumen for the wire guide. The tubular member may include a plurality of hollow wires.

In another embodiment, the present invention relates to a method of treating a vessel stenosis including the steps of deploying the minimally invasive device of this invention into a stenotic vessel wall and administering therapeutic or diagnostic agents through the hollow delivery struts into the stenotic vessel wall. The method may further include a step of deploying a medical device selected from the group consisting of stent, stent graft, balloon, and any other suitable medical device into a stenotic vessel.

In yet another embodiment, the present invention relates to a method of treating an aneurysm including the steps of deploying the minimally invasive device of this invention into an aneurismal vessel wall and administering therapeutic or diagnostic agents through the hollow delivery struts into the aneurismal vessel wall. The method may further include a step of deploying a medical device selected from the group consisting of stent, stent graft, balloon, and any other suitable medical device into an aneurismal vessel.

In yet a further embodiment, the present invention relates to a method of delivering therapeutic or diagnostic agents into a vessel wall. The method includes deploying a minimally invasive device, the device comprising an introducer tube, a tubular member having a proximal end, a distal end, and a first lumen extending therebetween, the tubular member being slidably disposed within the introducer tube; and a plurality of hollow delivery struts, each delivery strut adapted to pierce through inner most layers of the vessel wall and each, comprising at least one exit port and at least one stopper to prevent the delivery struts from piercing through the outer most layers of the vessel wall; said plurality of hollow delivery struts being disposed on the distal end of the tubular member, said hollow delivery struts being in fluid communication with the first lumen. The method also includes securing the hollow delivery struts at a first treatment location in the vessel wall and administering the therapeutic or diagnostic agents through the hollow delivery struts into the vessel wall at the first treatment location. The method may also include the step of securing the hollow delivery struts at plurality of treatment locations and administering therapeutic or diagnostic agents at plurality of treatment locations. The device may be temporarily deployed in a vessel.

Further aspects, features, and advantages of the invention will become apparent from consideration of the following description and the appended claims when taken in connection with the accompanying drawings.

BRIEF DESCRIPTION OF THE DRAWINGS

FIG. 1B is a side view of illustrative embodiment of the device of this invention;

FIG. 1C is a side view of an alternative embodiment of the device of this invention;

FIGS. 10A-D illustrate an exemplary method of treating vessel stenosis using the device of the present invention;

DETAILED DESCRIPTION OF THE DRAWINGS AND THE PRESENTLY PREFERRED EMBODIMENTS

Figure 1A:
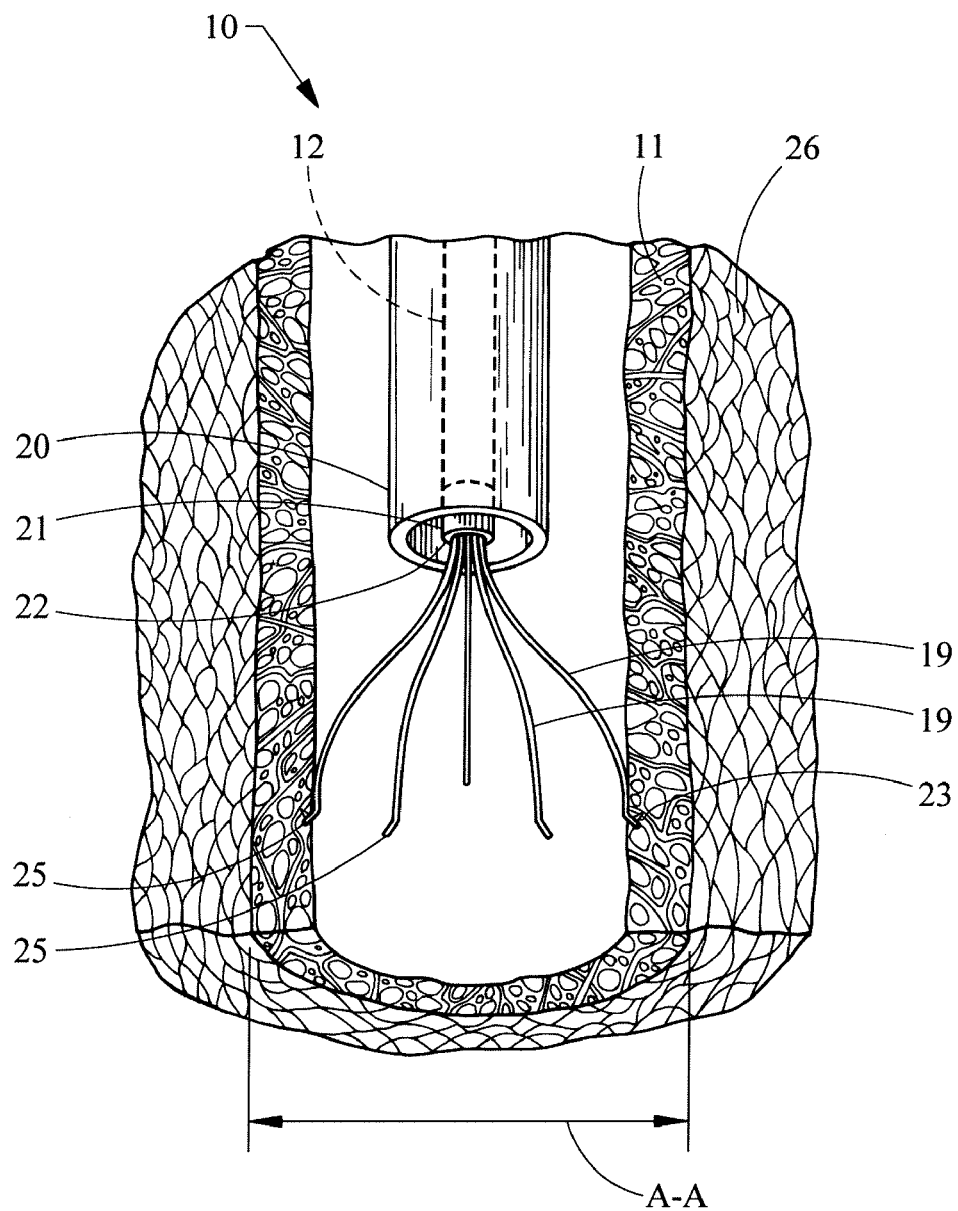
FIG. 1A depicts a side view of an exemplary minimally invasive device of this invention.

The present invention relates generally to minimally invasive devices and methods for administering therapeutic or diagnostic agents into vessel walls.

Unless otherwise defined, all technical and scientific terms used herein have the same meaning as commonly understood by one of ordinary skill in the art to which this invention pertains. In case of conflict, the present document, including definitions, will control. Preferred methods and devices are described below, although methods and devices similar or equivalent to those described herein can be used in the practice or testing of the present invention. All publications, patent applications, patents and other references mentioned herein are incorporated by reference in their entirety. The devices, methods, and examples disclosed herein are illustrative only and not intended to be limiting.

As used herein, the term "body vessel" means any tube-shaped body passage lumen that conducts fluid, including but not limited to blood vessels such as those of the human vasculature system, esophageal, intestinal, billiary, urethral and ureteral passages.

The term "vessel wall" refers to a protective, multi-layered biological barrier separating the fluid conducted by the body vessel from tissue surrounding the body vessel, such as extravascular tissue.

The term "extravascular tissue" refers to tissue surrounding a blood vessel.

The terms "about" or "substantially" used with reference to a quantity includes variations in the recited quantity that are equivalent to the quantity recited, such as an amount that is insubstantially different from a recited quantity for an intended purpose or function.

As used herein, "disposed" means placed or arranged in a particular order to define the relationship between elements or components of a device.

The term "tubular" refers to the general shape of a device or an element of the device, which allows the device to carry fluid along a distance or fit within a tubular structure such as an artery.

The term "prosthesis" refers to a substitute for a missing part of the body; may be a medical device.

The term "stent" refers to any device or structure that adds rigidity, expansion force or support to a tubular structure, such as vessel wall.

The term "stent graft" refers to a type of endoluminal prosthesis made of a tubular graft material and supported by at least one stent.

The term "proximal" refers to an area nearer to a point of reference such as an origin or a point of attachment. In this application the term proximal refers to an area nearer to the physician.

The term "distal" refers to an area further from a point of reference; further from a physician.

The term "healing" means replacing, repairing, healing, or treating of damaged or diseased tissues of a patient's body.

The terms "patient," "subject," and "recipient" as used in this application refer to any mammal, especially humans.

The term "therapeutic agent" refers to any pharmaceutically acceptable agent that is capable of producing a desired therapeutic biological effect in vivo (e.g., stimulation or suppression of cell division, proliferation, migration or apoptosis; stimulation or suppression of an immune response; anti-bacterial activity; etc.) to treat, prevent, and/or reverse conditions or diseases. Therapeutic agents include any biological agents, biologically active chemical compounds, pharmaceutical agents, biologically derived components such as cells (e.g., endothelial, smooth muscle, macrophages, stem cells, etc.), peptides, antibodies, and polynucleotides, and radiochemical therapeutic agents, such as radioisotopes.

The term "pharmaceutically acceptable," as used herein, refers to those compounds of the present invention which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms or prodrug forms, where possible, of the compounds of the invention.

Suitable therapeutic agents may include, for example, growth factors, antibiotics, anti-viral agents, analgesics, anti-inflammatories, both steroidal and non-steroidal, anti-neoplastics, anti-spasmodics including channel blockers, modulators of cell-extracellular matrix interactions including cell growth inhibitors and anti-adhesion molecules, enzymes and enzyme inhibitors, anticoagulants and/or antithrombotic agents, DNA, RNA, inhibitors of DNA, RNA or protein synthesis, compounds modulating cell migration, proliferation and/or growth, vasodilating agents, and other drugs commonly used for the treatment of injury to tissue. Combinations of these therapeutic agents may also be used.

In a first aspect, therapeutic agents typically used to inhibit bacterial or microbial activity may be selected. Suitable anti-infective agents include: anthracyclines (e.g., doxorubicin and mitoxantrone), fluoropyrimidines, folic acid antagonists (e.g., methotrexate), podophylotoxins (e.g., etoposide), camptothecins, and hydroxyureas. Particular nonlimiting examples of antimicrobial agents that may be used include acyclovir, amantadine, aminoglycosides (e.g., amikacin, gentamicin and tobramycin), amoxicillin, amoxicillin/Clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acidform) or non-pathogenic or "friendly" bacteria or other microbes that cause the production of hydrogen peroxide or other substances that kill or inhibit the growth of pathogenic microbes (e.g., lactobacillus).

In a second aspect, therapeutic agents typically used to treat or prevent an allergic or immune response may be selected, such as cytokine inhibitors (including humanized anti-cytokine antibodies, anti-cytokine receptor antibodies, recombinant (new cell resulting from genetic recombination) antagonists, or soluble receptors), various leucotriene modifiers (including zafirlukast, montelukast and zileuton), immunoglobulin E (IgE) inhibitors (including Omalizumab and secretory leukocyte protease inhibitors). Suitable immunomodulatory agents, such as sirolimus or rapamycin analogues, and derivatives including tacrolimus, everolimus and ABT-578 (zotarolimus) may also be used.

In a third aspect, therapeutic agents typically used to treat a tumor or cancerous lesion may be selected, such as antitumor agents (e.g., cancer chemotherapeutic agents, biological response modifiers, vascularization inhibitors, hormone receptor blockers, cryotherapeutic agents or other agents that destroy or inhibit neoplasia or tumorigenesis); alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, triazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU 11248, BMS-275291, COL-3, EMD 121974, IMC-1C11, IM862, TNP-470, celecoxib (Celebrex), rofecoxib (Vioxx), interferon alpha, interleukin-12 (IL-12), or any of the compounds identified in Science Vol. 289, Pages 1197-1201 (Aug. 17, 2000), which is expressly incorporated herein by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, chlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxanes (e.g., paclitaxel and derivatives thereof including docetaxel), and taxotere.

In a fourth aspect, therapeutic agents typically used to inhibit fibrosis may be selected. Examples of suitable fibrosis-inhibiting agents include an antimycotic agent, such as miconazole, sulconizole, parthenolide, rosconitine, nystatin, isoconazole, fluconazole, ketoconasole, imidazole, itraconazole, terpinafine, elonazole, bifonazole, clotrimazole, conazole, terconazole, piperazine, isoconazole, griseofulvin, bifonazole, econazole nitrate; croconazole, sertaconazole, omoconazole, flutrimazole, fluconazole, neticonazole, monohydrochloride, butoconazole, clotrimazole, or a collagen antagonist, such as benzenepropanamide, lufironil, or an analogue, or derivative thereof.

Therapeutic agents may be, for example, polynucleotides. Examples of polynucleotides, which are useful as therapeutic agents include, but are not limited to, nucleic acids and fragments of nucleic acids, including, for example, DNA, RNA, cDNA and recombinant nucleic acids; naked DNA, cDNA, and RNA; genomic DNA, cDNA or RNA; oligonucleotides; aptomeric oligonucleotides; ribozymes; anti-sense oligonucleotides (including RNA or DNA); DNA coding for an anti-sense RNA; DNA coding for tRNA or rRNA molecules (i.e., to replace defective or deficient endogenous molecules); double stranded small interfering RNAs (siRNAs); polynucleotide peptide bonded oligos (PNAs); circular or linear RNA; circular single-stranded DNA; self-replicating RNAs; mRNA transcripts; catalytic RNAs, including, for example, hammerheads, hairpins, hepatitis delta virus, and group I introns which may specifically target and/or cleave specific RNA sequences in vivo; polynucleotides coding for therapeutic proteins or polypeptides, as further defined herein; chimeric nucleic acids, including, for example, DNA/RNA hybrids, RNA/RNA hybrids, DNA/RNA hybrids, DNA/peptide hybrids, and RNA/peptide hybrids; DNA compacting agents; and gene/vector systems (i.e., any vehicle that allows for the uptake and expression of nucleic acids), including nucleic acids in a non-infectious vector (i.e., a plasmid) and nucleic acids in a viral vector.

In an exemplary embodiment, chimeric nucleic acids may include, for example, nucleic acids attached to a peptide targeting sequences that directs the location of the chimeric molecule to a location within a body, within a cell, or across a cellular membrane (i.e., a membrane translocating sequence ("MTS")).

In another embodiment, a nucleic acid may be fused to a constitutive housekeeping gene, or a fragment thereof, which is expressed in a wide variety of cell types.

In certain embodiments, polynucleotides delivered by non-viral methods may be formulated or associated with nanocaps (e.g., nanoparticulate $CaPO_4$), colloidal gold, nanoparticulate synthetic polymers, and/or liposomes. In one embodiment, polynucleotides may be associated with QDOT™ Probes (www.qdots.com).

In other embodiments, polynucleotides useful as therapeutic agents may be modified so as to increase resistance to nucleases, e.g. exonucleases and/or endonucleases, and therefore have increased stability in vivo. Exemplary modifications include, but are not limited to, phosphoramidate, phosphothioate and methylphosphonate analogs of nucleic acids (see also U.S. Pat. Nos. 5,176,996; 5,264,564; and 5,256,775).

In certain embodiments, therapeutic agent may be a polynucleotide that is contained within a vector. Suitable vectors include, for example, viral vectors or vectors derived from viral sources, such as adenoviral vectors, herpes simplex vectors, papilloma vectors, adeno-associated vectors, retroviral vectors, pseudorabies virus, alpha-herpes virus vectors, and the like. A thorough review of viral vectors, particularly viral vectors suitable for modifying nonreplicating cells, and how to use such vectors in conjunction with the expression of polynucleotides of interest can be found in the book Viral Vectors: Gene Therapy and Neuroscience Applications Ed. Caplitt and Loewy, Academic Press, San Diego (1995).

Vectors may be, for example, non-infectious vectors, or plasmids. Suitable non-infectious vectors, include, but are not limited to, mammalian expression vectors that contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17.

Therapeutic agents may be, for example, inhibitors of DNA, RNA, or protein synthesis.

In one embodiment, therapeutic agents may also include c-Jun N-terminal kinase (JNK) inhibitors. Exemplary JNK inhibitors include those described in U.S. Provisional Pat. Application No. 60/881,879, filed on Jan. 23, 2007.

In another embodiment, therapeutic agents may include matrix metalloproteinases (MMPs) inhibitors, including endogenous inhibitors, such as tissue inhibitors of MMPs (TIMPs) and α-macroglobulins, and synthetic inhibitors, such as chelating agents (e.g., EDTA and 1,10-phenanthroline), peptides, antibodies, and the like. Agents that would enhance function of TIMPs may also be used as therapeutic agents.

In yet another embodiment, any suitable tetracycline, including tetracycline per se, or tetracycline-derivative compounds, preferably doxycycline hydrate, doxycycline aureomycin and chloromycin may be used as therapeutic agents. Tetracycline compounds may include CMTs (CMT that lack the dimethylamino group at position 4 of the ring structure of tetracycline, including 4-dedimethylaminotetracycline (CMT-1), 4-dedimethylamino-5-oxytetracycline, 4-dedimethylamino-7-chlorotetracycline (CMT-4), 4-hydroxy-4-dedimethylaminotetracycline (CMT-6), 5a,6-anhydro-4-hydroxy-4-dedimethylaminotetracycline, 6-demethyl-6-deoxy-4-dedimethylaminotetracycline (CMT-3; COL-3), 4-dedimethylamino-12a-deoxytetracycline (CMT-7), and 6-α-deoxy-5-hydroxy-4-dedimethylaminotetracycline (CMT-8); tetracyclines modified at the 2 carbon position to produce a nitrile, e.g., tetracyclinonitrile; 6-α-benzylthiomethylenetetracycline, the mono-N-alkylated amide of tetracycline, 6-fluoro-6-demethyltetracycline, and 11α-chlorotetracycline).

In another embodiment, therapeutic agents may be beta blockers. Beta blockers include acebutolol, atenolol, betaxolol, bisoprolol, carteolol, carvedilol, esmolol, labetolol, metoprolol, nadolol, penbutolol, pindolol, propranolol, and timolol.

Other therapeutic agents may include cyclooxygenase-2 (COX-2) inhibitors; angiotensin-converting enzyme (ACE) inhibitors; glucocorticoids; nitric acid synthase (NOS) inhibitors; other anti-inflammatories; anti-oxidants; and cellular adhesion molecules (CAMs). COX-2 inhibitors include Celecoxib, Rofecoxib, Valdecoxib, Etoricoxib, Parecoxib, all of which are available in pharmacological preparations. Additionally, COX-2 inhibition has been demonstrated from herbs, such as green tea, ginger, turmeric, chamomile, Chinese gold-thread, barberry, baikal skullcap, Japanese knotweed, rosemary, hops, feverfew, and oregano; and other agents, such as piroxican, mefenamic acid, meloxican, nimesulide, diclofenac, MF-tricyclide, raldecoxide, nambumetone, naproxen, herbimycin-A, and diaryl hydroxyfuranones.

In a further embodiment, therapeutic agents may include non-steroidal anti-inflammatory agents (NSAIDs), such as ketoralac tromethamine (Toradol), indomethacin, ketorolac, ibuprofen and aspirin among others. Additionally, steroidal based anti-inflammatories, such as methylprednisolone, dexamethasone or sulfasalazine may be provided. Other suitable anti-inflammatory agents include cyclosporine A and azathioprine.

Therapeutic agents may also be anti-oxidants, such as curcumin, vitamins, and vitamin constituents, such as α-tocopherol and β-carotene.

Therapeutic agents may be ACE inhibitors, such as captopril, enalapril, losartan and lisinopril and the active forms of several ACE inhibitor prodrugs on the market.

In a further embodiment, therapeutic agents may also include inhibitors of cathepsins. Cathepsin inhibitors may be classified as cysteine proteinase inhibitors, aspartic proteinase inhibitors, or serine proteinase inhibitors. For a comprehensive review of cathepsin inhibitors see Kim W. and Kang K, "Recent developments of cathepsin inhibitors and their selectivity," Expert Opin. Ther. Patents (2002) 12(3), pp 419-432. The medical devices comprising cathepsin inhibitors were previously described in U.S. Provisional Pat. Application No. 60/755,961, filed Jan. 3, 2006; PCT Application No. PCT/US2006/048865, filed Dec. 22, 2006; U.S. patent application, 11/809,779, filed Jun. 1, 2007; and U.S. Provisional patent application, 60/952,828, filed Jun. 1, 2007, disclosures of which are incorporated herein by reference in their entirety.

Other therapeutic agents, such as the NOS inhibitors, including aminoguanidine may also be included.

In another embodiment, therapeutic agents may include elastin-stabilizing compounds, such as phenolic tannin compounds. Phenolic tannin compounds were previously described in U.S. Provisional Pat. Application No. 60/799,608, filed May, 10, 2006, and U.S. patent application, 11/800,217, field on May 4, 2007, disclosures of which are incorporated herein in their entirety.

Additional therapeutic agents may include those described in U.S. Pat. No. 5,834,449; U.S. Pub. Nos. 2005/0266043 A1, published on Dec. 1, 2005, and 2006/0004441 A1, published on Jan. 5, 2006, which are incorporated herein by reference.

Also included are therapeutic agents capable of inhibiting in-stent restenosis, including for example, antiproliferative and immunosuppressive agents. For example, both paclitaxel and sirolimus have been previously shown to be very effective in blocking in-stent restenosis. Agents that promote endothelial cell regrowth and vascular healing may also be included. Examples of these and other therapeutic agents that may be used for restenosis inhibition are listed in Table 1 below (adopted from Camenzind E and De Scheerder I K, "Local Drug Delivery for Coronary Artery Disease," Martin Dunitz, an imprint of the Taylor & Francis Group plc, Chapter 19: "Overview of potential drugs to inhibit in-stent restenosis," pages 171-172 (2005)).

Further, these substances may also be combined with any of the implantable structural devices described below (stents, expanders, etc.) that may be implanted or delivered prior to or after the treatment with the device of this invention.

Figures 4A, 4B:
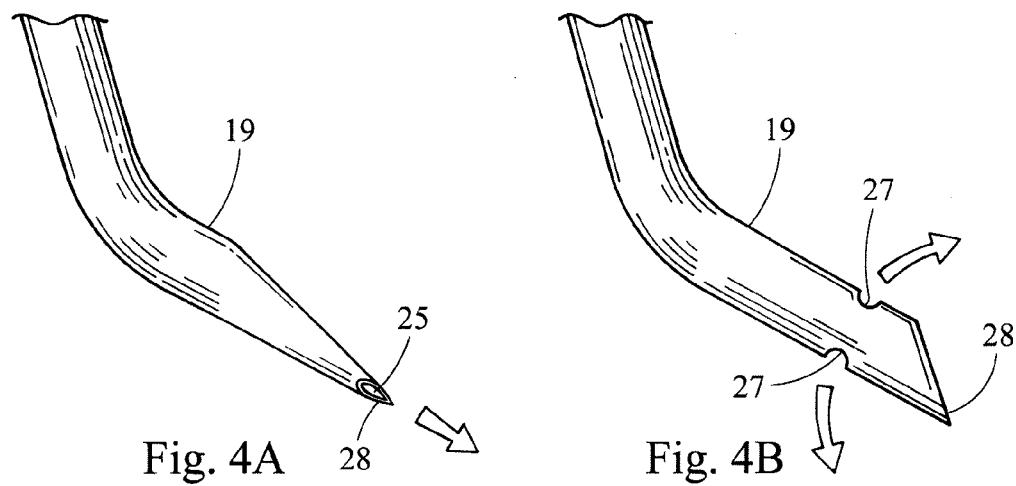
FIGS. 4A-B are cross-sectional views of illustrative embodiments of the hollow delivery struts.

Referring to FIGS. 1A-B, illustrative minimally invasive device 10 of the present invention is described. The device 10 includes an introducer tube 20, such as a catheter, a tubular member 12, such as a catheter, a hollow wire or plurality of hollow wires, having a proximal end 13, a distal end 14 and a lumen 12' extending between the distal and proximal ends 13, 14 of the tubular member 12, the tubular member 12 being slidably disposed in the introducer tube 20. Exemplary catheters and their methods of manufacture include those previously described, for example in U.S. Pub. No. 2004/0236346 A1, which is incorporated herein in its entirety. The tubular member 12 may be about 30 cm long or longer and is adapted to be percutaneously and transluminally inserted into a body vessel. The device 10 also includes a plurality of hollow delivery struts 19 disposed on the distal end 14 of the tubular member 12 and being in fluid communication with the lumen of the tubular member 12. The hollow delivery struts are designed to readily pierce through the inner most layer of the vessel wall 11, to enable delivery of therapeutic or diagnostic agents into the vessel wall 11. For example, the tips 25 of the hollow delivery struts 19 may include piercing tips 28 (FIGS. 4A and 4B). The hollow delivery struts also include means (not shown) for mechanically preventing movement of the delivery struts and preventing the struts from piercing through the outer most layers of the vessel wall 11 and going into the tissue 26 surrounding the body vessel. In addition, the hollow delivery struts include at least one exit port (not shown). These elements will be discussed in more detail below.

As will be discussed below, in one alternative embodiment, the hollow delivery struts may include at least one fixation element 23 for fixing or anchoring the device in the vessel wall. The fixation elements may include, but are not limited to, barbs, hooks, anchors, projections, or the like.

TABLE 1

| Antithrombotic | Antioxidants | Antiinflammatory Immunomodulator | Antiproliferative | Migration Inhibitor ECM-modulator | Promote Healing and re-endothelialization |
| --- | --- | --- | --- | --- | --- |
| Hirudin | Omega 3 fatty acids | Dexamethasone | QP-2, Taxol | Batimastat | BCP671 |
| Glycoprotein IIb/IIIa | Vitamin E | M-prednisolone | Actinomycine | Prolyl hydroxylase inhibitors | VEGF |
| Heparin | Melatonin Tempamine | Interferon-γ1b Leflunomide | Methothrexate Angiopeptin | Halofuginone C-proteinase inhibitors | Estrogen |
| | | Sirolimus Tacrolimus Everolimus Mycophenolic acid Mizoribine | Vincristine Mitomycine Statins c-myc antisense Abbott ABT-578 | Probucol | |
| | | Cyclosporine Tranilast | RestenASE 2-chloro-deoxyadenosine PCNA ribozyme | | |

The term "diagnostic agent" refers to any agent suitable for diagnostic use, such radio-isotopes or contrast agents.

As may be applied to any of the therapeutic or diagnostic agent listed previously or below, these substances may be combined with any one or more drug-releasing devices or molecular constructs such as polymers, collagen, gels, implantable osmotic pump devices, etc. to permit their release over an extended period of time once deposited.

The proximal end 13 of the tubular member 12 may be coupled to a handle 15. In one embodiment, handle 15 includes distal portion 15', which may be joined to an introducer tube 20, and a proximal portion 15" which may be joined to the hub 17. Alternatively, the hub 17 may be slidably disposed about the tubular member 12. A guide wire component 18 may extend through hub 17 through the distal end of the tubular member 12 to guide the delivery of the device within the vessel. Referring to FIG. 1A, the tubular member 12 is arranged for sliding movement in an introducer tube 20.

In one embodiment, referring still to FIGS. 1A and 1B, the proximal end 13 of the tubular member 12 may be coupled to handle 15 and distal end 14 may have an endcap 21. In one embodiment, plurality of hollow delivery struts 19 may be affixed to distal endface 22 of the endcap 21. In one embodiment, the endcap 21 having the hollow delivery struts 19 disposed thereon may be configured to screw into the distal end 14 of the tubular member 12, as shown in FIG. 1C.

Alternatively, the plurality of the hollow delivery struts may be directly bonded to or disposed on the distal end of the tubular member 12 without the use of an endcap.

The device 10 may be comprised of any suitable material, such as a superelastic material, stainless steel wire, cobalt-chromium-nickel-molybdenum-iron alloy, cobalt-chrome alloy, or MRI-compatible alloys. It is understood that the device 10 may be formed of any other suitable material that will result in a self-opening or self-expanding device, such as shape memory alloys. Shape memory alloys have a property of becoming rigid that is, returning to a remembered state, when heated above a transition temperature. A shape memory alloy suitable for the present invention may comprise Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one alternate embodiment, the device 10 may be made from Nitinol with a transition temperature that is slightly below normal body temperature of humans, which is about 98.6° F. In one embodiment, when the tubular member 12 and hollow delivery struts 19 of the device 10 are deployed in a body vessel and exposed to normal body temperature, the alloy of the device 10 will transform to austenite, that is, the remembered state, which for one embodiment of the present invention is the expanded configuration when the device 10 is deployed in the body vessel. To remove the device, the tubular member 12 and the struts 19 are pulled back mechanically into the lumen of the introducer tube 20 or the introducer tube 20 is pushed over the tubular member 12 and the struts 19.

In another alternate embodiment, the device 10 may be made from Nitinol with a transition temperature that is above normal body temperature of humans, which is about 98.6° F. In one embodiment, when the tubular member 12 and hollow delivery struts 19 of the device 10 are deployed in a body vessel and exposed to normal body temperature, the device 10 is in the martensitic state so that the device 10 is sufficiently ductile to bend or form into a desired shape, which for the present invention is an expanded configuration. To remove the device, the tubular member 12 and the struts 19 are pulled back mechanically into the lumen of the introducer tube 20 or the introducer tube 20 is pushed over the tubular member 12 and the struts 19.

In one embodiment, the device 10 may include at least one hollow delivery strut 19. In one embodiment, the device 10 may include a plurality of hollow delivery struts 19. For example, in another embodiment, the device may include at least two hollow delivery struts. In yet another embodiment, the device may include at least three hollow delivery struts. In a further embodiment, the device may include at least four hollow delivery struts. In a further embodiment, the device may include at least five hollow delivery struts. In yet another embodiment, the device may include at least six hollow delivery struts. In a further embodiment, the device may include at least seven hollow delivery struts. In a further embodiment, the device may include at least eight hollow delivery struts. In another embodiment, the device may include as many hollow delivery struts as mechanically possible. In one embodiment, the device may include for example, up to twelve hollow delivery struts.

The hollow delivery struts may be made from materials, including cobalt-chromium alloys, stainless steel materials, spring metals, shape memory alloy wires, or other suitable materials, an may have an inner diameter of about 0.002" to about 0.071" and an outer diameter from about 0.004" to about 0.095", and be from about 1 mm to about 5 cm long. However, other sizes and lengths of hollow delivery struts are also contemplated and may be used with the device of this invention.

Each delivery strut 19 is disposed on the distal end 14 of the tubular member and is in fluid communication with the lumen 12' of the tubular member 12. The hollow delivery struts 19 may be disposed on the tubular member 12, for example as discussed above, by directly bonding the delivery struts to the distal end of the tubular member, by an endcap having hollow delivery struts disposed thereof adapted to screw onto the distal end of the tubular member 12, or other methods that would be known to those skilled in the art.

Figure 1D:
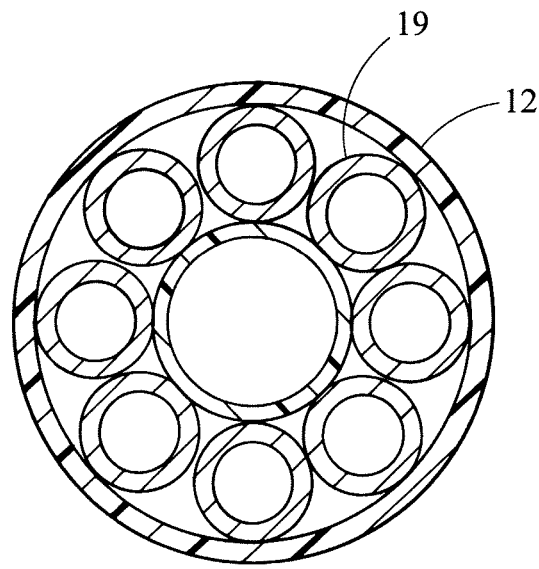
FIG. 1D is a cross section of a device of the present invention depicting illustrative configuration of the hollow delivery struts.

In one embodiment, the hollow delivery struts may be disposed on the distal end of the tubular member in a circular pattern, as illustrated in FIG. 1D. Alternatively, the hollow delivery struts may be arranged in a different pattern, for example to cover more or less of the circumference of the tubular member or the endcap, depending upon the intended application of the device 10.

Figure 2:
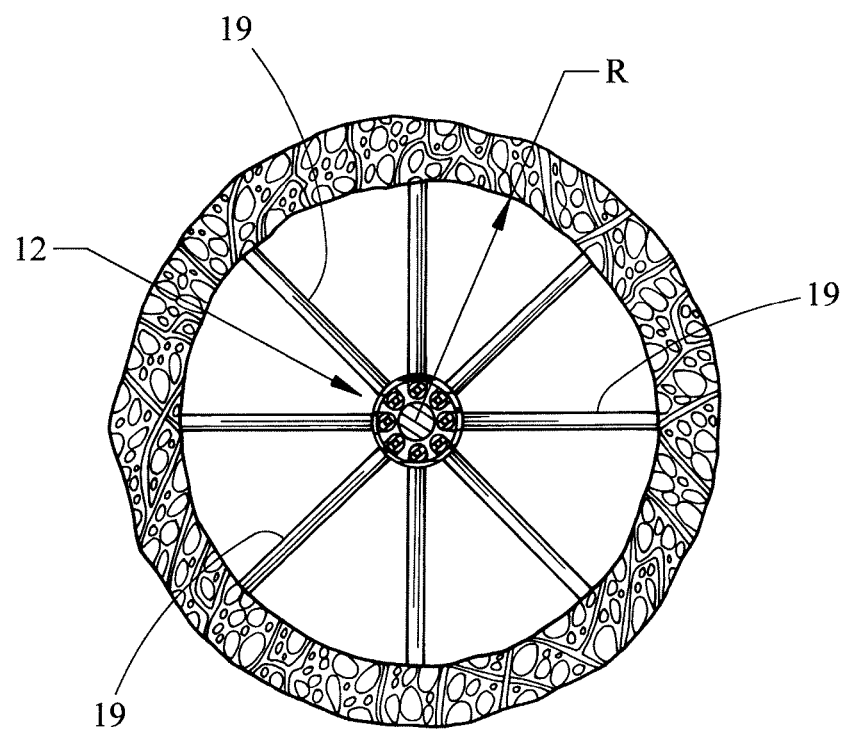
FIG. 2 is a cross-sectional view of a blood vessel of FIG. 1 taken along line A-A.

FIG. 2 depicts one example of a configuration or pattern formed by the hollow delivery struts 19 and the tubular member 12 relative to the radial axis R. FIG. 2 depict the pattern at substantially equal angular space relative to each other. This type of pattern provides an even distribution between the hollow delivery struts 19 to the blood flow and vessel wall. However, it is to be understood that each of the sets of hollow delivery struts 19 may be configured in any other suitable manner to radial axis R.

Figure 3A:
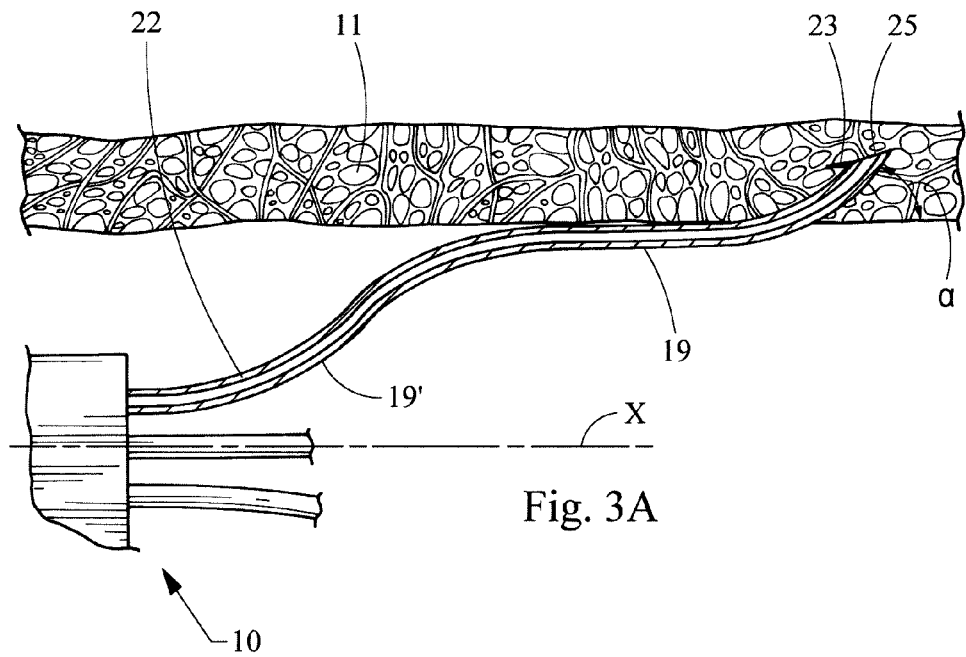
FIG. 3A is a cross-sectional view of one illustrative embodiment of a delivery strut.
Figure 3B:
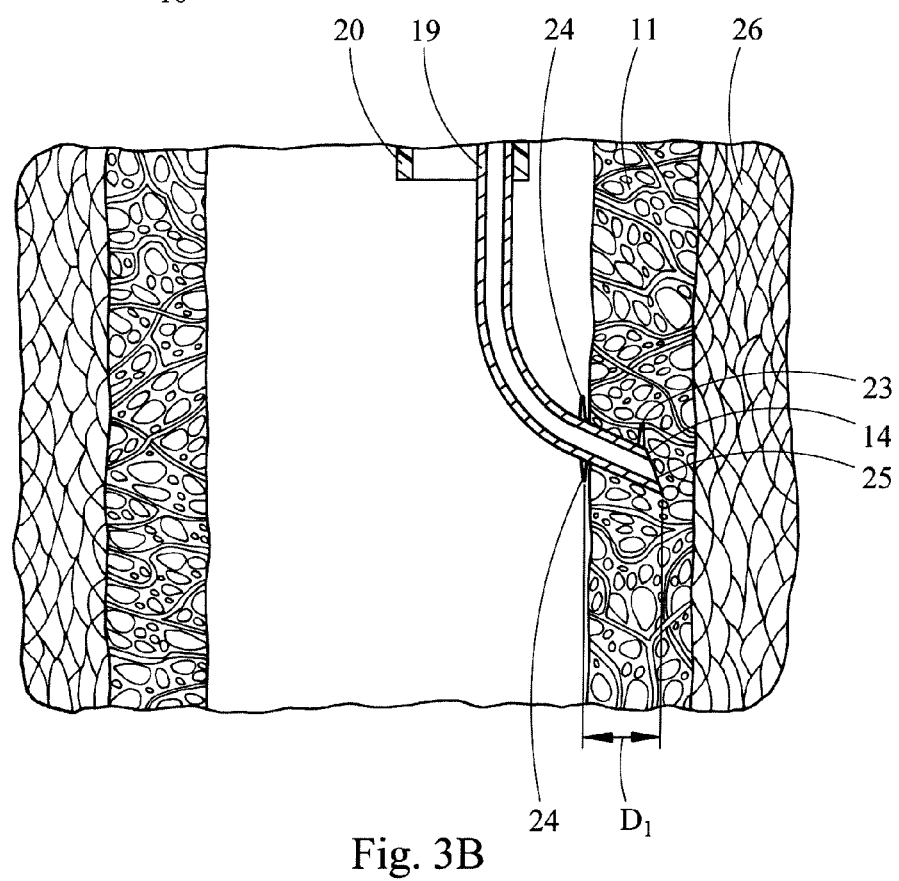
FIG. 3B is a cross-sectional view of one alternative embodiment of a delivery strut.

In one embodiment, as illustrated in FIGS. 3A-B, each delivery strut 19 is hollow and may include an arcuate segment having a soft S-shape (shown in cross-section). S-shape, however, is not necessary for proper functioning of the device of this invention. Each arcuate segment may be formed with first curved portion 19' that is configured to softly bend away from the longitudinal or central axis X of the device 10. Due to the soft bends of each arcuate segment, a prominence or a point of inflection on the delivery strut 19 is substantially avoided to aid in non-traumatically engaging the vessel wall 11. In one embodiment, the hollow delivery struts have beveled tips that form about 45° angle α with the vessel wall. This angle allows for easy retraction and retrieval of the hollow delivery struts.

In the expanded state, each arcuate segment may extend arcuately along a longitudinal axis (as shown in FIG. 1) and linearly relative to a radical axis R (as shown in FIG. 2) from the first end 22 to the tips 25 of the hollow delivery struts 19. The hollow delivery struts 19 extend linearly relative to the radial axis and avoid entanglement with other hollow delivery struts.

In some embodiments, the hollow delivery struts may be needles. For example, a plurality of fixed-length hollow needles may be disposed on the distal end of the tubular member or on the endface of the endcap. These needles are in fluid communication with the tubular member and may be extended to pierce through the inner most layers of the vessel wall for delivery of therapeutic or diagnostic agents into the vessel wall. Exemplary devices and methods of delivery of the devices including needles were previously described in U.S. Pat. No. 6,217,554.

Each hollow delivery strut 19 also includes means 24 for mechanically preventing the movement of the hollow delivery struts 19 and preventing the delivery struts 19 from piercing through the outer most layer of the vessel wall 11 and going into the tissue 26 surrounding the body vessel. Means 24 for mechanically preventing movement of the hollow delivery struts 19 may include a "stopper." A stopper refers to a structural element attached or disposed on or configured as part of (by bonding, welding, gluing, crimping, laser cutting, or by any mechanical or chemical fixation, etc.) the distal ends 14 of the hollow delivery struts 19 at a specified distance D1 from the tip 25 of the delivery strut 19 that can bring to a halt or cause to stop the delivery strut from passing through the hole made in the vessel wall and piercing through the outer most layers of the vessel wall. Stoppers may include, but are not limited to a single or multiple square pieces or a ring, of metal, polymer or other material that is mechanical in nature. In one embodiment, D1 may be from about 5 mm to about 0.5 mm. Alternatively, the D1 may be from about 5 mm to about 1 mm. In yet another alternative embodiment, the D1 is 1 mm. Multiple stoppers may be included on the hollow delivery struts at same or varying distances from the tips 25 of the delivery struts 19 depending on the placement of the stopper. In one embodiment, stoppers may include a ring of material attached to or disposed on the outer surface of the hollow delivery struts 19 at a specified distance D1 from the tips 25 of the hollow delivery struts.

Figure 3E:
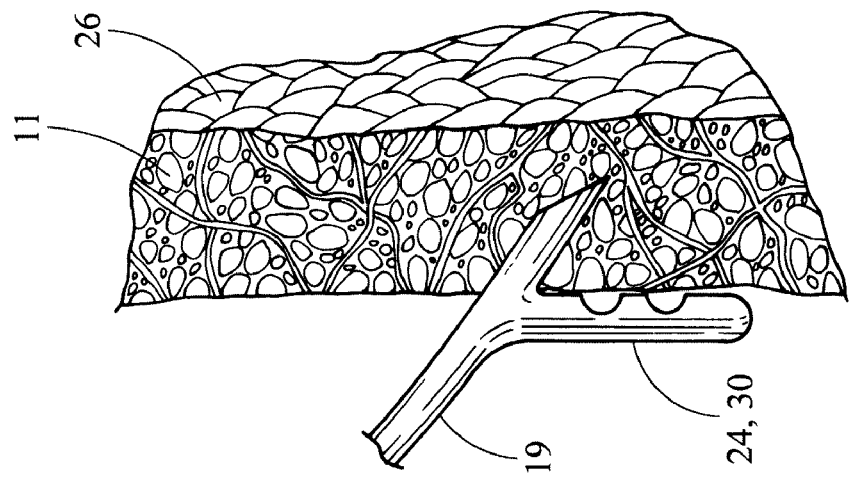
FIGS. 3C-3E depict alternative embodiments of stoppers.
Figure 3D:
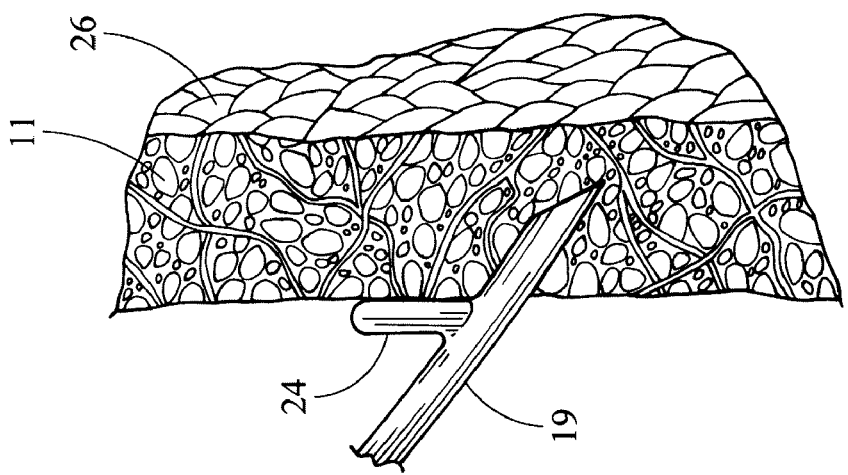
Figure 3C:
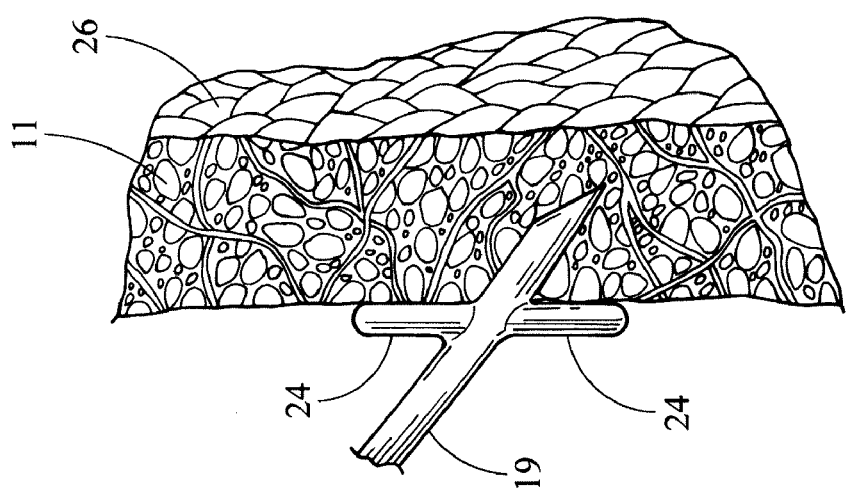

FIGS. 3C-3E illustrate alternative embodiments of stoppers.

Alternatively, the tubular member 12 may be configured to enable the clinician to adjust the depth to which tips 25 of hollow delivery struts 19 penetrate the vessel wall 11 by controlling relative motion between tubular member 12 and introducer tube 20 using handle 15. For example, the handle 15 may include gradiations that provide correspondence between relative motion of handle portions and extension of hollow delivery struts 19.

As shown in FIG. 4A-B, the hollow delivery struts 19 also include at least one exit port 27 for delivery of therapeutic or diagnostic agents into a vessel wall 11. Multiple exit ports may also be present. The presence of multiple exit ports may allow the therapeutic or diagnostic agents to exit the hollow delivery struts 19 with greater uniformity of drug delivery. Multiple exit ports may also help with reducing the pressure at the distal end of the delivery struts and allow for delivery of therapeutic or diagnostic agents into the vessel wall 11. Also, a greater amount of therapeutic or diagnostic agents may be delivered in a shorter period of time via multiple exit ports. As illustrated, for example in FIG. 4A, the hollow delivery struts 19 may terminate at an exit port at a tip 25 of the delivery strut 19. In another embodiment, shown in FIG. 4B, exit ports may be arranged around the distal circumference of the hollow delivery struts 19, resulting in "side" exit ports. Side exit ports may be separated, or spaced, an appropriate distance along the body of the distal ends of the delivery struts and the length of the distal ends of the hollow delivery struts in proportion to the delivery struts' French size. Such configuration would be desired to increase distribution points for delivering of therapeutic or diagnostic agents. In one embodiment, side exit ports may be adjacent to each other to allow for a quick and efficient delivery of therapeutic agents. In yet another embodiment, the hollow delivery struts may include exit ports at the distal tip of the delivery struts as well as side exit ports.

In one embodiment, the side exit ports may further aid in keeping the hollow delivery struts in place in the vessel wall while the therapeutic agents are being delivered into the vessel wall. As such, these side exit ports may function as fixation elements for the device. In yet another embodiment, the side exit ports may function as stoppers to prevent movement of the delivery struts and preventing the delivery struts from piercing through the outer most layers of the vessel wall and going into the tissue 26 surrounding the body vessel.

In certain embodiments, the tubular member 12 and/or other components of the device 10, such as the delivery struts 19, may include (or be coated with) echogenic marks or dimples formed thereon to provide reflections of ultrasound waves during ultrasonography, e.g., two-dimensional or three-dimensional ultrasonography. In one embodiment, the echogenic marks are formed circumferentially about the tubular member 12. The echogenic layer may include hollow echogenic particles for enhanced ultrasonography. After deployment of the device in a body vessel of a patient, the device 10 may be monitored using ultrasonography. The tubular member 12 may be identified by way of the echogenic marks thereon and my further assist in determining the location of the hollow delivery struts 19 during delivery or retrieval of the device 10. The surface may also be modified or treated in any manner known in the art to create echogenic features.

In other embodiment, the tubular member 12 and/or other components of the device 10, such as the delivery struts 19, may include additional coating layers providing enhanced identifying features. For example, the hollow delivery struts may include at least one radiopaque coating. The radiopaque coating may be a polymeric coating, ceramic coating, or a noble metal coating for enhanced fluoroscopy. In one embodiment, the radiopaque coating may be noble metal coating. Noble metals that may be used as the radiopaque coating include gold, platinum, iridium, palladium, or rhodium, or a mixture thereof. The radiopaque coating may be applied to the device by any suitable means, e.g., spraying or dipping. In another embodiment, the radiopaque coating may be polymeric coating, such as polyethylene, polypropylene, or any other suitable polymeric material.

In other embodiments, the tubular member 12 and/or other components of the device 10, such as the hollow delivery struts 19, may include a coating, such as anti-thrombogenic coating and/or a fibrinolytic coating, disposed thereon for reduced blood clots and endotheliosis in the body vessel. In one embodiment, the coating is an anti-thrombogenic agent that acts to inhibit formation of blood clots or a fibrolytic agent to dissolve fibrin by enzymatic action. The coating may include heparin, streptokinase, urokinase, alteplase, anistreplase, prourokinase, alfimeprase, lumbrokinase, nattokinase, boluoke, serrapeptase, and euglobulin or any other suitable anti-thrombogenic agent or fibrinolytic agent. For example, as known, heparin is a medication typically used to reduce the likelihood of blood clots from forming in a patient's body. The coating may be applied to the components of the device 10 by any suitable means, such as by spraying or dipping. The coating may then be cured for a predetermined time known to those skilled in the art.

In certain embodiments, the hollow delivery struts 19 may also include at least one fixation element 23 for fixing or anchoring the struts in the vessel wall 11. The fixation elements 23 can include structural features, such as barbs, hooks, anchors, projections, or the like that maintain the hollow delivery struts in position following deployment in the body lumen. The art provides a wide variety of structural features that are acceptable for use in the medical device, and any suitable structural feature can be used. Furthermore, barbs can also comprise separate members attached to the hollow delivery struts by suitable attachment means, such as welding and bonding. For instance, barbs can be formed by V-shaped cuts transversing the thickness of a flat metal frame, which are bent outward to form the barb. In some embodiments, the number, arrangement, and configuration of the integral barbs can vary according to design preference and the clinical use of the device. The barbs can have any suitable shape, including points or "fish hook"-like configurations. The barbs may or may not penetrate the vessel wall, depending on their design and other factors, including the thickness and type of covering used. In one embodiment, the barbs may pierce through the inner most layers of the vessel wall to function as piercing tips.

In one embodiment shown in FIG. 3A, the hollow delivery struts 19 terminate at anchoring hooks 23 that will anchor in the vessel wall 11 when the tubular member 12 and the struts 19 of the device 10 are deployed at a treatment location. Other fixation elements include, for example barbs. The hollow delivery struts 19 are configured to move between an expanded state for engaging the anchoring hooks 23 within the vessel wall and a collapsed state for retrieval or delivery of the tubular member 12 and struts 19.

When the device is deployed in a blood vessel, the anchoring hooks may engage the walls of the blood vessel to define a first axial portion to secure the device in the blood vessel wall. The anchoring hooks prevent the device from migrating from the delivery or treatment location where it has been deposited. In this embodiment, although some damage to the tissue may occur during the retrieval of the tubular member 12 and struts 19 into the introducer tube 20, the damage is relatively minor and compensated for by delivery of the therapeutic agents.

In certain embodiments, the hollow delivery struts are shaped and dimensioned such that, when the struts are freely expanded, the device may have a diameter of between about 3 mm and 50 mm, depending on the type of the body vessel, and a length of between about 5 mm and 7 cm in this embodiment. For example, the device may have a diameter of about 35 mm and a length of about 5 cm. The hollow delivery struts have sufficient spring strength that when the device is deployed, the piercing tips will pierce through the inner most layers of the vessel wall and the anchoring hooks will anchor into the vessel wall.

Figure 5A:
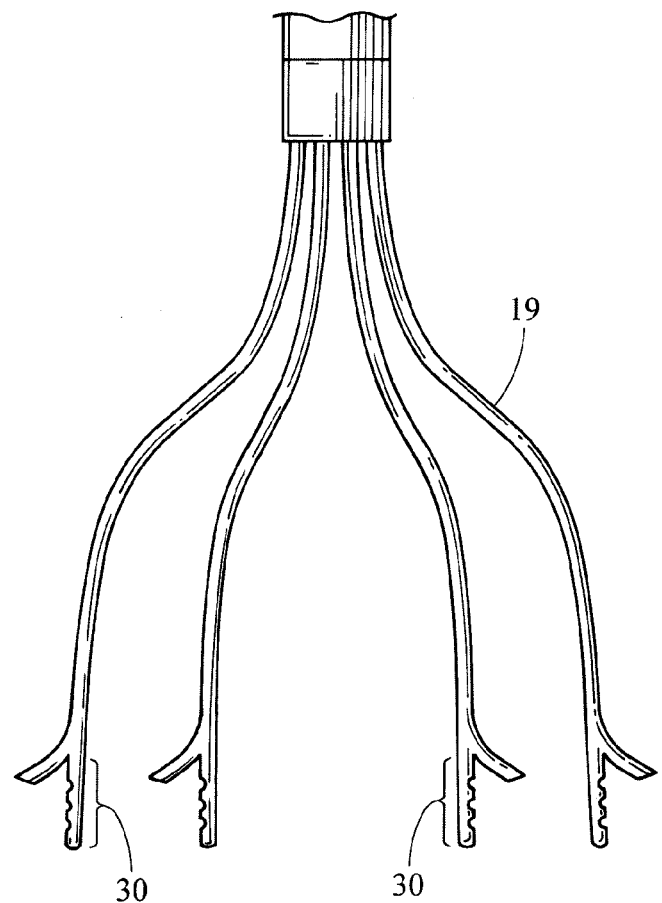
FIGS. 5A-B depict alternative embodiments of the device of this invention.
Figure 5B:
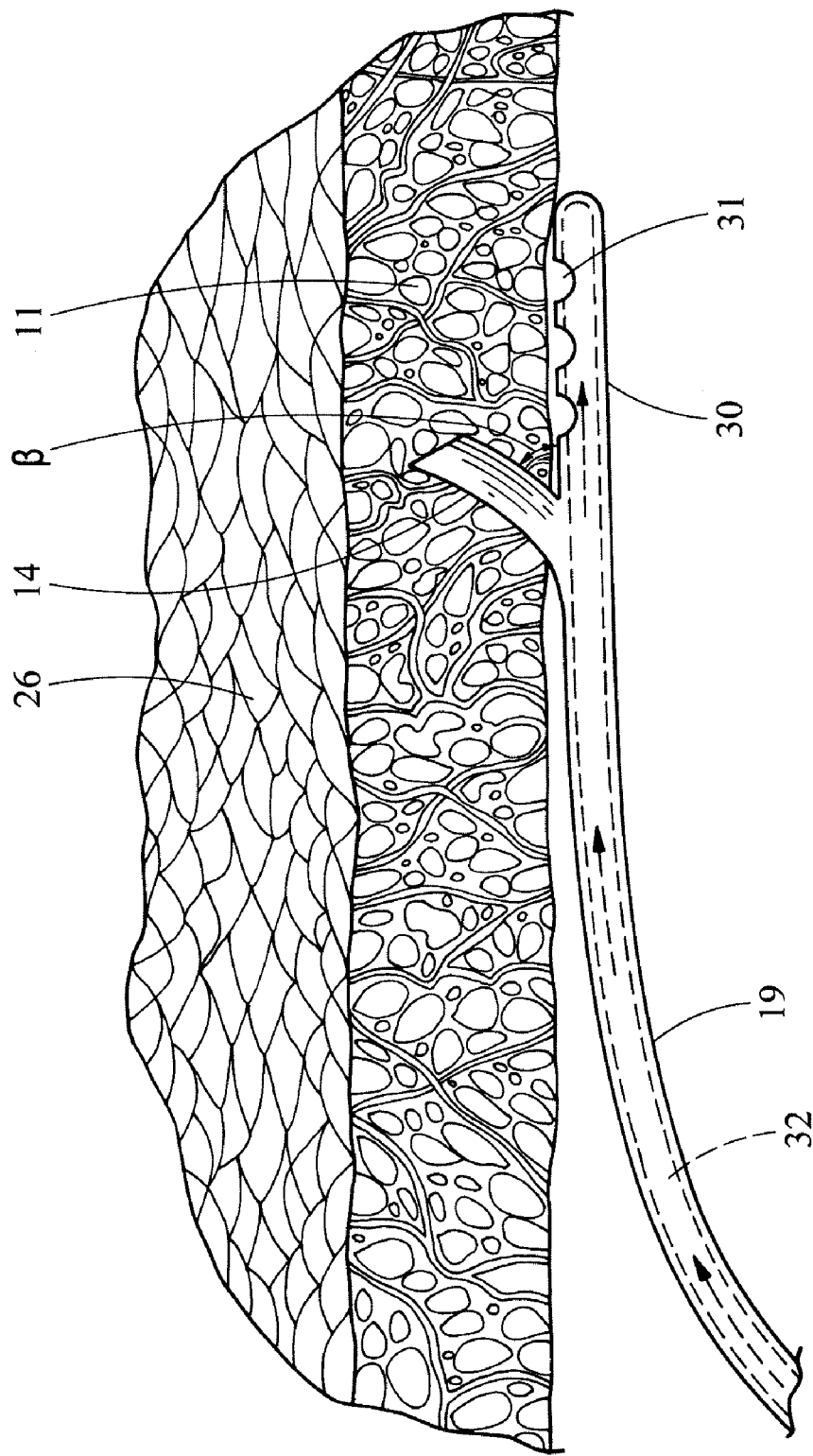

In certain embodiments, illustrated in FIGS. 5A-5B, the hollow delivery struts 19 may include "extensions" 30 at the distal ends of the hollow delivery struts 19. When the device is in an expanded state, the extensions 30 line up parallel to the inner vessel wall and form an angle β from about 30° to about 60° with the distal portion 14 of the hollow delivery struts 19 without piercing through the inner most layers of the vessel wall. In a preferred embodiment, the extensions 30 form an angle β of approximately 45° with the distal portion 14 of the hollow delivery struts 19 without piercing through the inner most layers of the vessel wall. In one embodiment, extensions 30 may include at least one exit port 31 and are in fluid communication with the lumens 32 of the delivery struts 19. In such instance, in addition to the therapeutic agents being delivered into the vessel wall through the hollow delivery struts 19, therapeutic or diagnostic agents may also be delivered in close proximity to and along the inner vessel wall near the treatment location.

In one alternative embodiment, extensions 30 may be included with the device to enhance stability of the device at the treatment location. In such instance, extensions 30 may not need to be in fluid communication with the hollow delivery struts and may not need to include exit ports for drug delivery.

In yet another alternative embodiment, the extensions 30 may function as stoppers.

Figure 6A:
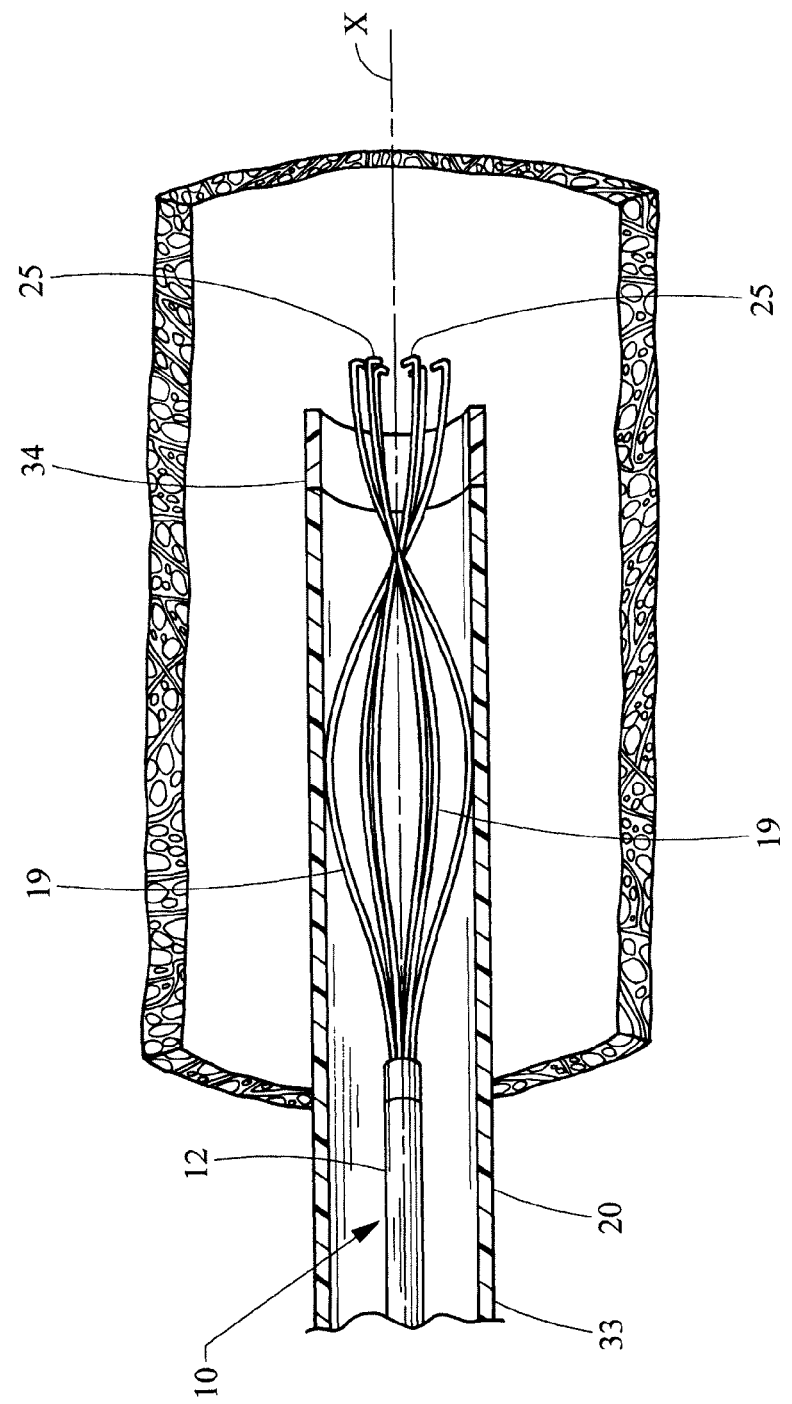
FIG. 6A is a cross-sectional view of a blood vessel in which the introducer tube includes illustrative device of this invention in a collapsed state.

The introducer tube 20 for delivery or retrieval of the tubular member and struts may be any suitable introducer (delivery or retrieval) tube 20 known in the art (i.e., "introducer tube," such as a catheter), the tube having a proximal end 33 and a distal end 34 and a lumen extending between the proximal and distal ends 33, 34 of the introducer tube 20 (FIG. 6A). In one embodiment, the tubular member 12 and struts 19 are slidably disposed within the introducer tube 20 for deployment into the body vessel wall or retrieval from the body vessel wall. For example, the introducer tube 20 may have an inside diameter of between about 4.5 French and about 16 French. In another embodiment, the introducer tube 20 may have an inside diameter between about 6.5 French and about 14 French.

FIG. 6A illustrates the tubular member 12 and struts 19 in a collapsed state slidably disposed in introducer tube 20 for delivery or retrieval. In one embodiment shown, the device 10 may be shaped for each delivery strut 19 to cross another delivery strut relative to the longitudinal axis X. As a result, in the collapsed state, the tips 25 are configured to invert or inwardly face the longitudinal axis X for retrieval and delivery of the tubular member 12 and struts 19. This inverted or inwardly facing configuration of the tips 25 allows for simplified delivery and retrieval of the device.

In the collapsed state, each delivery strut 19 may be configured to cross another delivery strut relative to the longitudinal axis X such that the arcuate segments, first curved portions or second curved portions, occupy a first diameter. In this embodiment, the first diameter is greater than a second diameter occupied by the anchoring hooks for device delivery and retrieval. It has been found that the first diameter of the arcuate segments serves to reduce radial force from the sheath or blood vessel on the tips and or fixation elements during removal of the device from a patient. Reducing the radial force on the fixation elements assists in preventing the anchoring hooks from scraping, scratching, or tearing the inner wall of a sheath during removal of the device from a patient.

In alternative embodiments, the first diameter occupied by the arcuate segments, first curved portions or second curved portions, is equal or less than the second diameter occupied by the anchoring hooks.

Figure 6B:
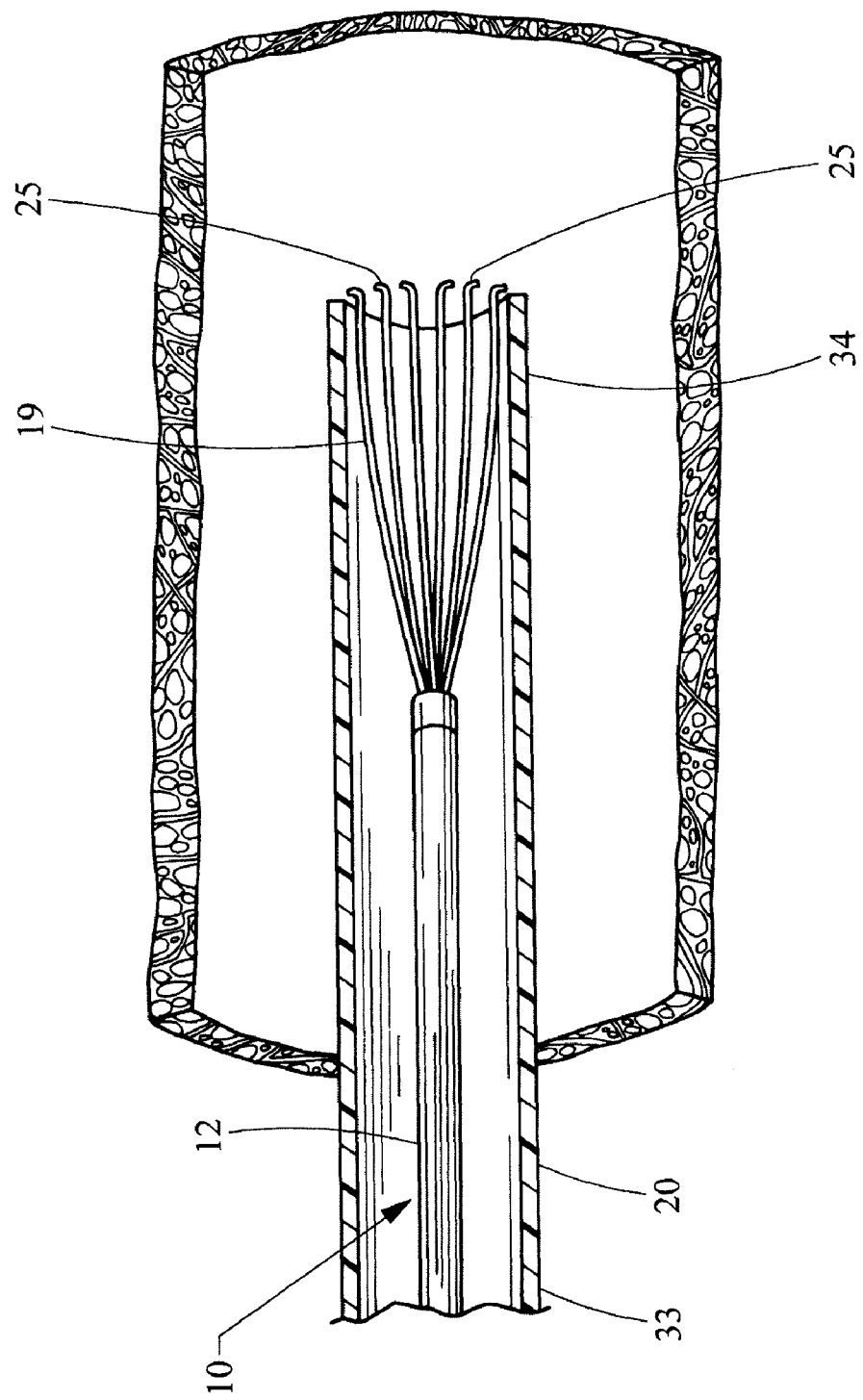
FIG. 6B is a cross-sectional view of a blood vessel in which the introducer tube includes another illustrative device of the present invention.

Also, in some embodiments hollow delivery struts 19 may not cross each other when collapsed in the introducer tube 20 (FIG. 6B). For example, when retraced back into the introducer tube 20, the hollow delivery struts 19 may be closely bunched together, and assume the delivery position substantially parallel to a longitudinal axis of the introducer tube 20. In the delivery position, the introducer tube 20 prevents tips 25 of the hollow delivery struts from puncturing the patient's vasculature during insertion or withdrawal of the device 10.

Figure 7:
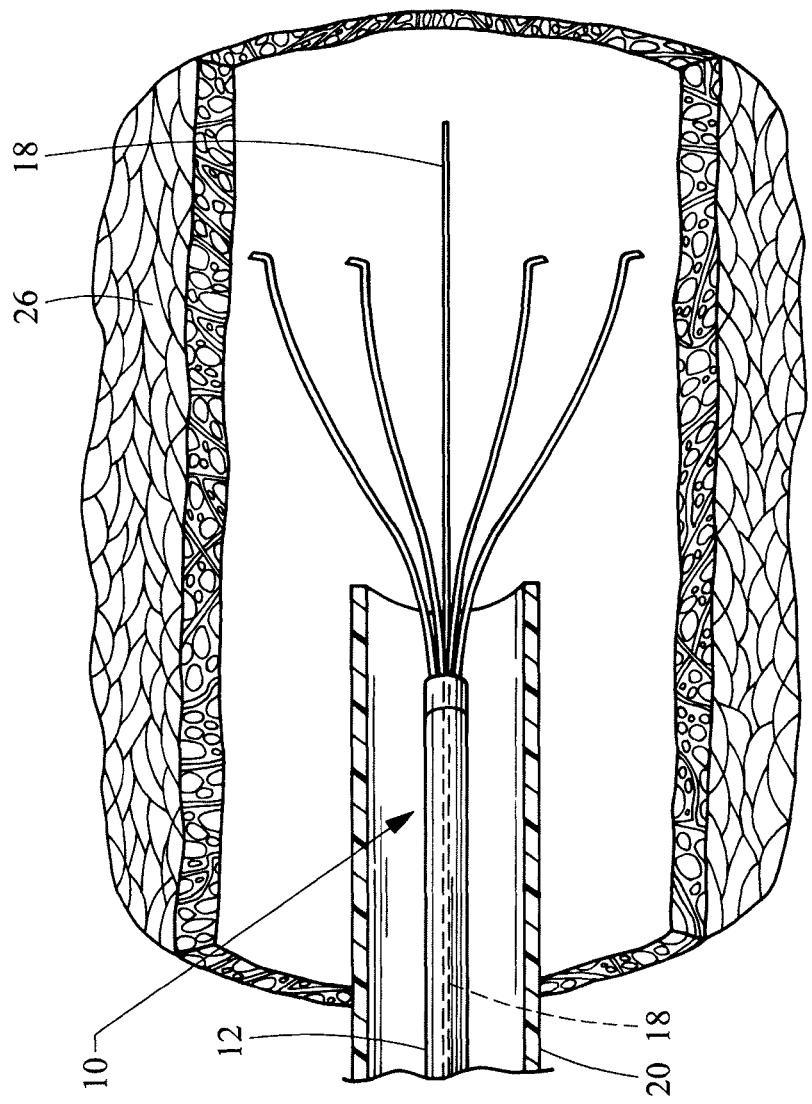
FIG. 7 is a cross-sectional view of a blood vessel in which the introducer tube includes illustrative device of this invention as an "over the wire" device.

In one embodiment, referring to FIG. 7, the device may also include a wire guide component 18 for guiding the device into the vessel.

Figure 8A:
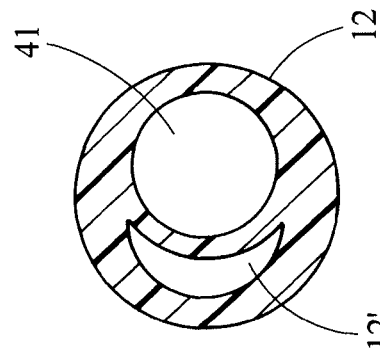
FIGS. 8A-B depict illustrative embodiments of an "over the wire" device of this invention.
Figure 8B:
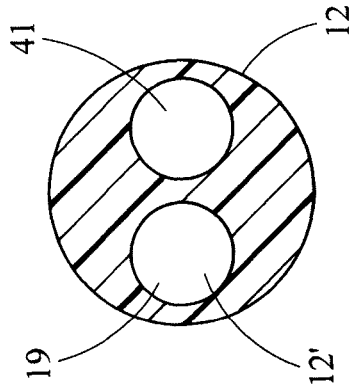

One example of a suitable wire guide component 18 may be a stiff wire guide, such as one made from stainless steel or nitinol. The wire guide may be inserted into the lumen prior the delivery of introducer tube 20 and withdrawn following the insertion of the introducer tube prior to deployment of the tubular member 12 and struts 19. In certain embodiments shown in FIGS. 8A and 8B, which are cross sections of the tubular member at the endcap) the tubular member 12 may be configured as "over the wire system." For example, the tubular member 12 may include a separate guide wire lumen 41. In this embodiment, the device 10 may be inserted over the wire guide without the necessity of withdrawing the wire guide 18 prior to delivering the device 10. A drug lumen 12' of the tubular member 12 is also shown.

Figure 9A:
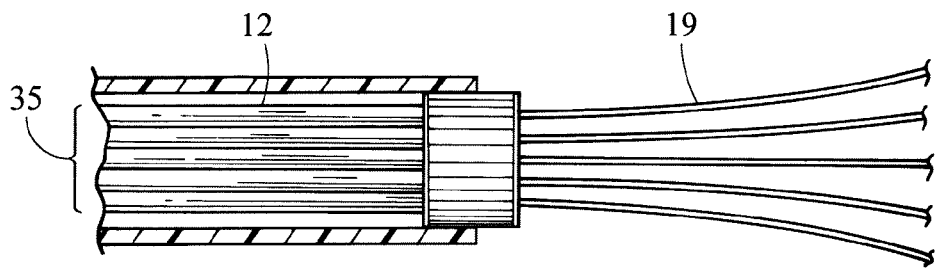
FIGS. 9A-C illustrate alternative embodiments of the device of this invention.
Figure 9B:
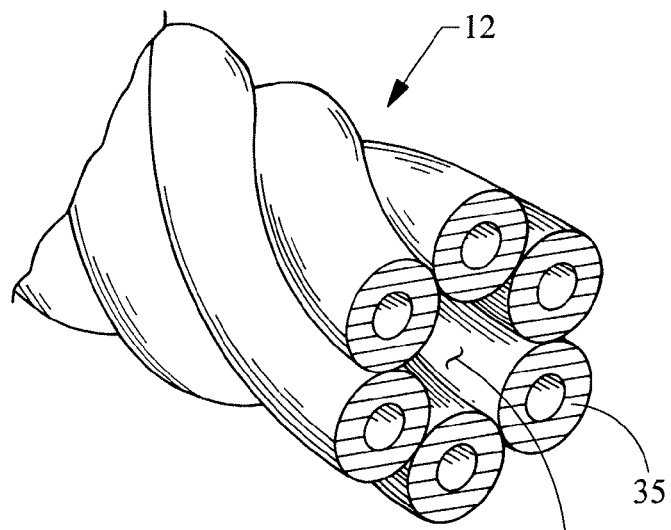
Figure 9C:
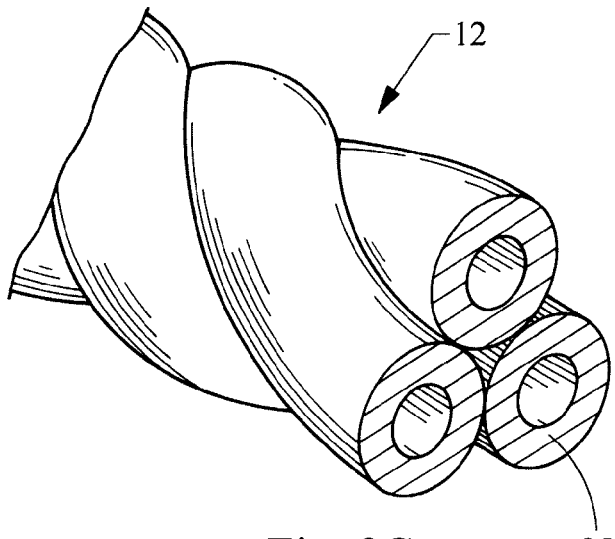

In certain embodiments, the tubular member may be formed from a plurality of hollow wires 35 in a parallel configuration (as shown, for example, in FIG. 9A) or twisted into a cable tubing-like configuration (as shown, for example, in FIGS. 9B-9C). In FIG. 9B, for example, the tubular member 12 is formed from six individual hollow wires twisted together creating a lumen 36. In this embodiment, lumen 36 may be for the wire guide component 18 (another example of over-the-wire system). In FIG. 9C, for example, the tubular member 12 is formed from three individual hollow wire twisted together so that no lumen is created. Each of the individual hollow wires 35 is in fluid communication with the hollow delivery struts 19, as shown in FIG. 9C.

In one embodiment, the tubular member extends from the handle, which allows for continued retention of the device 10 after the deployment in the blood vessel 11 and retrieval back into the introducer tube 20.

Because it may be desired to deploy the device 10 in several treatment locations in the injured or diseased blood vessel 11, it is advantageous to continuously retain the device of this invention 10, without permanently deploying it at a specific treatment location. By doing so, the tubular member 12 and delivery struts 19 of the device 10 may be retrieved back into introducer tube 20 quickly, the introducer tube 20 with the tubular member 12 and delivery struts 19 advanced to the next treatment location and delivered at a second treatment location. Following the delivery of the therapeutic or diagnostic agents, the tubular member 12 and delivery struts 19 may again be quickly retrieved back into the introducer tube 20 and the device 10 advanced to the next treatment location, etc.

In one embodiment, syringe 40 (FIG. 1B), containing therapeutic agents may be used to inject therapeutic agents into the tubular member 12, such as catheter, hollow wires or the like, or to the individual hollow wires. Since the tubular member is in fluid communication with the hollow delivery struts, the therapeutic or diagnostic agents once injected into the lumen of the tubular member are also delivered into the hollow delivery struts and ultimately into a vessel wall of a patient. As shown in FIG. 1B, the syringe may be coupled to the handle 15.

Once the struts 19 are placed at a treatment location, therapeutic or diagnostic agents are injected into the tubular member 12 and the hollow delivery struts 19 for delivery into the wall 11 of a body vessel.

The device of this invention has numerous uses and applications, including treatment of coronary artery disease, vessel stenosis, aneurysm, including aortic aneurysm, such as abdominal aortic aneurysm, or aortic dissection. Other uses are also contemplated and will be apparent to those skilled in the art.

Figures 10A, 10B:
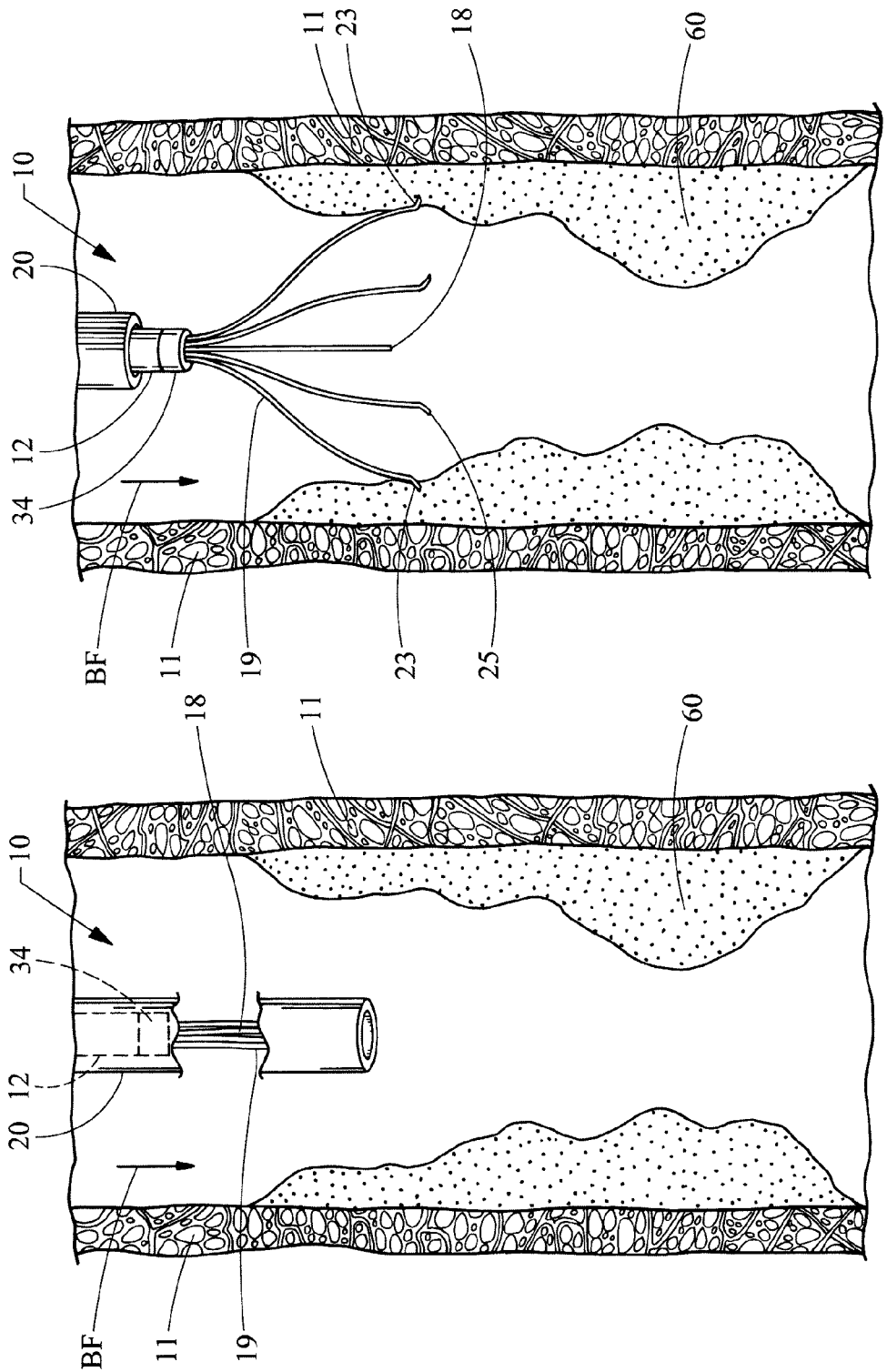

In one embodiment, referring to FIG. 10A, the device 10 is being temporarily delivered to a severely stenotic blood vessel. The direction of the blood flow BF is indicated in FIG. 10A by arrow that is referred to as BF. The tubular member 12 and struts 19 are inserted through the proximal end 33 of the introducer tube 20 (not shown) with the tips 25, fixation elements 23 (not shown) and hollow delivery struts 19 leading for delivery via, for example, femoral vein or jugular vein of a patient until the tubular member 12 and struts 19 reach the distal end 34 of the introducer tube 20 placed at a desired, first treatment location. In one embodiment, a wire guide 18 could be inserted into the vessel prior to delivering the device.

FIG. 10B illustrates the tubular member 12 and struts 19 expanded after being temporarily deployed into a severely stenotic blood vessel in this embodiment. Once the device 10 is delivered to the desired treatment location, the tubular member 12 and struts 19 are deployed in a vessel. When the tubular member 12 and struts 19 are fully expanded in the body vessel, the piercing tips 28 pierce through the inner most layers of the vessel wall and the fixation elements 23 of the hollow delivery struts 19 engage the vessel wall 11. The stoppers (not shown) prevent the device 10 from piercing all the way through the vessel wall (i.e., though the outer most layers of the vessel wall) and going into the surrounding tissue. The fixation elements 23 at the ends of the hollow delivery struts 19 are shown as being anchored in the stenosis of the blood vessel 60 at a first treatment location. In one embodiment, the anchoring hooks include barbs. The fixation elements 23, such as anchoring hooks, of the delivery struts 19 fix or anchor the device at the treatment location in the vessel, preventing the device 10 from moving with the blood flow through the vessel.

As discussed previously, the barbs may function to retain the device at the first location of deployment, which is a first treatment location, until after the therapeutic agents are delivered into the stenosis of the blood vessel and allow delivery of therapeutic or diagnostic agents into the stenotic blood vessel. Once the device is positioned at the first treatment location, therapeutic agents may be injected for delivery into the vessel wall. One example of a therapeutic agent that may be delivered to treat vessel stenosis includes paclitaxol that prevents or inhibits cell proliferation and as a result halts progression of vessel stenosis.

As seen in FIG. 10C, the tubular member 12 is positioned upstream from the treatment location at which the anchoring hooks are anchored in the vessel. When the struts of device 10 are to be removed or re-positioned at a different treatment location, a physician can pull at the handle to withdraw the tubular member 12 and struts 19 back into the introducer tube 20 and as a result the struts 19 are dislodged from the vessel wall 11 and inserted back into the introducer tube 20. In an alternative embodiment, to withdraw the tubular member 12 and struts 19, the physician may push the hub 17 joined to the introducer tube 20 so that the introducer tube 20 is pushed over the tubular member 12 and struts 19 ("re-sheeting").

Once the tubular member 12 and struts 19 are in the introducer tube 20, the tube may be moved to another treatment location downstream from the first treatment location and the tubular member 12 and struts 19 deployed at a second treatment location, as shown in FIG. 10D. Once at the second treatment location, the therapeutic agents may be injected into the device for delivery into the vessel wall.

The steps of this process may be repeated several times depending on the number of desired treatment locations, severity of the stenosis and other pertinent factors.

Figure 11A:
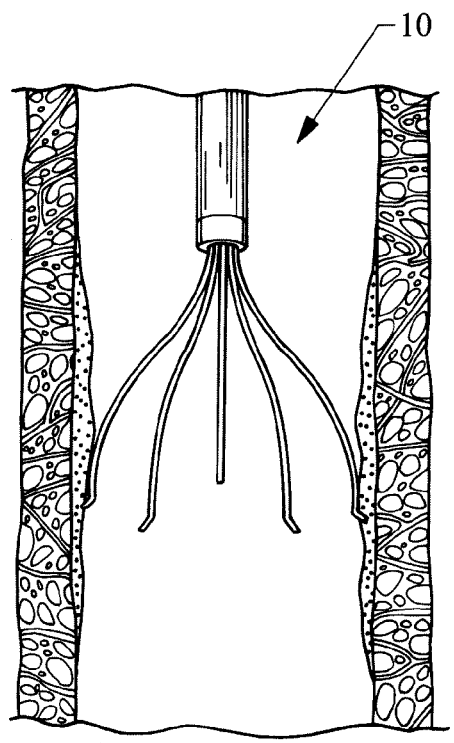
FIGS. 11A-B depict another exemplary method of treating vessel stenosis with the device of the present invention and a stent.
Figure 11B:
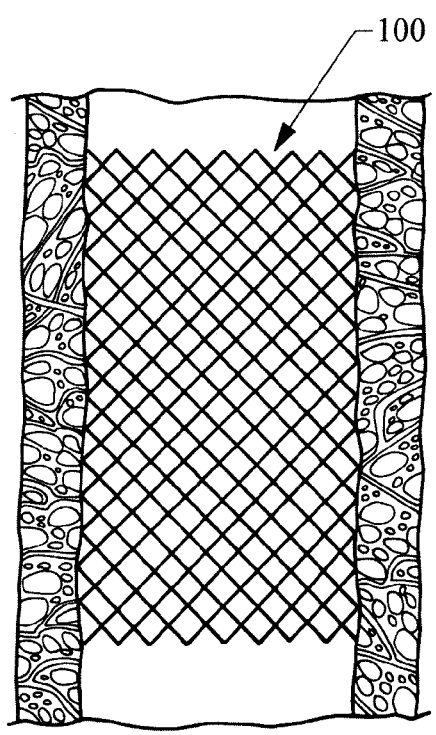

In one embodiment, shown in FIGS. 11A-B, following the treatment with the device 10 of the present invention, a medical device 100, such as a stent, stent graft, or a balloon, may be delivered for permanent or temporary implantation in the body vessel.

In another embodiment, a medical device 100, such as a stent or a stent graft, may be delivered to a diseased body vessel prior to delivering the tubular member 12 and struts 19 of the device of the present invention 10 directly proximal and/or distal to the already placed medical device 100. Various methods for delivering medical devices will be known to those skilled in the art.

In a further alternative embodiment, a medical device 100, such as a stent or s stent graft may be delivered to a diseased body vessel prior to delivering the tubular member 12 and struts 19 of the device of the present invention 10 to the treatment location and delivery of the therapeutic or diagnostic agents into the vessel wall.

In a further embodiment, a balloon angioplasty may be performed either prior or after delivery of the therapeutic agents with the device of this invention.

Various types of medical devices may be used prior to or following the treatment using the device of the present invention. The medical devices may have any suitable configurations. In one embodiment, the medical device may be an implantable medical device, such as a graft, stent, or stent graft. In one embodiment, the implantable medical device may be an endoluminal medical device, which may be placed inside a lumen of a patient. For example, a stent graft may be placed inside a body vessel. Alternatively, an implantable device may be a medical device, such as a vascular wrap, which may be placed on the outside of a body lumen during an open surgery. In yet another embodiment, the medical device may be a delivery device, such as a balloon catheter. Brief description of some exemplary medical devices is provided below. Other configurations are also contemplated.

In one aspect, the medical device may be a stent. The stent may have any configuration adapted to maintain the lumen of a body vessel at a desired degree of patency. Stents are well known in the art. One example of a stent includes a self-expanding nickel-titanium stent for percutaneous implantation sold under the tradename ZENITH®, commercially available from Cook, Incorporated (Bloomington, Ind.). Other examples include a Wallstent variety stent or a Giant-urco-Roubin, Palmaz-Shatz, Wiktor, Strecker, Cordis, AVE Micro Stent, Igaki-Tamai, Millenium Stent, Cook-Z® Stent or Zilver Stent. Some exemplary stents are also disclosed in U.S. Pat. Nos. 5,292,331; 6,090,127; 5,133,732; 4,739,762; and 5,421,955.

In another aspect, the medical device may be a stent graft. In this embodiment, the stent may include one or a plurality of radially-expanding stents such as Z-STENTS®, which are available from Cook, Incorporated (Bloomington, Ind.). The graft material may be a woven or non-woven fabric, such as Dacron®, or may be a polymeric material such as expanded polytetrafluoroethylene (ePTFE), or may be a reconstituted or naturally derived collagenous material, including extracellular matrix material, such as small intestine submucosa (SIS).

PCT Application WO 98/53761, hereby incorporated by reference in its entirety, discloses a number of details concerning stents, stent grafts, and a method for implanting stent grafts into the human body.

Figure 12:
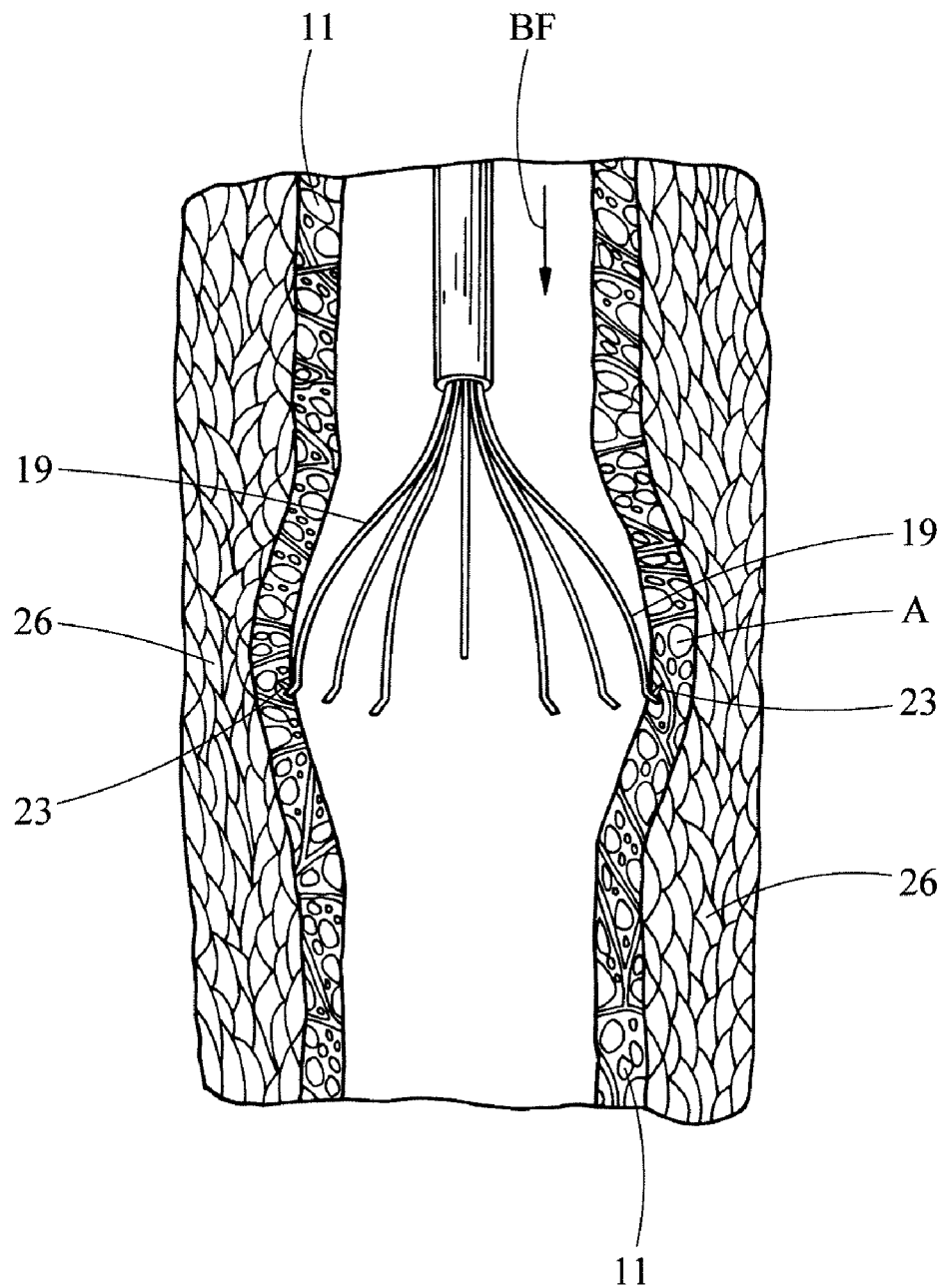
FIG. 12 illustrates one exemplary method of treating an aneurysm using the device of the present invention.

FIG. 12 illustrates the tubular member 12 and struts 19 of the device 10 of this invention fully expanded after being temporarily deployed in a blood vessel with an aneurysm A. The direction of the blood flow BF is indicated in FIG. 12 by the arrow that is labeled BF. The fixation elements 23 at the ends of the hollow delivery struts 19 are shown as being anchored in the inner lining of the blood vessel wall 11. The fixation elements may include barbs. The barbs function to anchor and retain the device at the treatment location. The spring biased configuration of the delivery struts 19 further causes the piercing tips to pierce through the inner most layers of the vessel wall and the fixation elements 23 to engage the vessel wall 11 and fix or anchor the device at the treatment location. The means for mechanically preventing movement of the struts, i.e., stoppers, at the distal ends of the hollow delivery struts (not shown) prevent the struts from going through the outer most layers of the vessel wall and into the tissue 26 surrounding the body vessel. Once the struts 19 are placed at the desired treatment location, therapeutic agents, such as for example, cells (autologous smooth muscle cells, myofibroblasts), bulking agents, such as SIS (in a particle or gel form) or drugs may be delivered into the vessel wall. These therapeutic agents may prevent or inhibit further weakening or thinning of the vessel wall and progression of the aneurysm or reduce the aneurysm. Bulking agents may be injected into the vessel wall to strengthen the aneurismal sac.

Following the delivery of the therapeutic or diagnostic agents into the aneurismal vessel wall, the tubular member 12 and the hollow delivery struts 19 of the device 10 may be retrieved back into the introducer tube 20 and advanced to another treatment location within the aneurismal body lumen.

In one further embodiment, the invention may also be a kit that includes the device 10 of this invention and at least one of a wire guide, a handle, and/or syringe. Also, in one embodiment, the introducer tube 20 may be separate from the tubular member 12 and the hollow delivery struts 19.

It is therefore intended that the foregoing detailed description be regarded as illustrative rather than limiting, and that it be understood that it is the following claims, including all equivalents, that are intended to define the spirit and scope of this invention.

The invention claimed is:

1. A method of delivering therapeutic or diagnostic agents into a vessel wall, comprising:
   i) deploying a minimally invasive device, comprising:
      an introducer tube;
      a tubular member having a proximal end, a distal end, and a first lumen extending therebetween, the tubular member being slidably disposed within the introducer tube; and
      a plurality of hollow delivery struts disposed on the distal end of the tubular member and in fluid communication with the first lumen, each hollow delivery strut adapted to pierce through inner most layers of the vessel wall and each, comprising
         at least one exit port, and
         at least one stopper to prevent the delivery struts from piercing through the outer most layers of the vessel wall, the at least one stopper extending from the hollow delivery strut;
      an extension at a distal portion of at least one of the hollow delivery struts, the extension comprising at least one other exit port in fluid communication with the hollow delivery strut and;
   ii) securing the hollow delivery struts at a first treatment location in the vessel wall;
   iii) administering the therapeutic or diagnostic agents through the hollow delivery struts into the vessel wall at the first treatment location.

2. The method of claim 1, comprising securing the hollow delivery struts at plurality of treatment locations and administering therapeutic or diagnostic agents at plurality of treatment locations.

3. The method of claim 2, further comprising retrieving the hollow delivery struts into the introducer tube prior to advancing the minimally invasive device to a second treatment location.

4. The method of claim 2, wherein securing comprises anchoring the minimally invasive device in the vessel wall with at least one fixation element selected from the group consisting of barbs, hooks, anchors, and projections.

5. The method of claim 1, wherein the minimally invasive device is temporarily deployed in a vessel.

6. The method of claim 1, comprising administering the therapeutic or diagnostic agents along the inner wall near the treatment location through the extension.

7. The method of claim 1, wherein the extension is the stopper.

8. The method of claim 1, the stopper extending from the hollow delivery strut and positioned at a distance of from about 5 mm to about 0.5 mm from a distal tip of the hollow delivery strut.

9. The method of claim 1, wherein each delivery strut comprises multiple exit ports.

10. The method of claim 9, wherein the administering the therapeutic or diagnostic agents is through the multiple exit ports.

11. The method of claim 1, wherein administering the therapeutic or diagnostic agents through the hollow delivery struts comprises injecting the therapeutic or diagnostic agents into the tubular member and the hollow delivery struts.

12. The method of claim 1, further comprising providing a wire guide prior to the deploying of the minimally invasive device.

13. The method of claim 1, further comprising deploying a medical device selected from the group consisting of stent, stent graft, and balloon.

14. The method of claim 13, wherein deploying the medical device is following the treatment with the minimally invasive device.

15. The method of claim 13, wherein deploying the medical device is prior to delivering the minimally invasive device, wherein the delivering the minimally invasive device is proximal, within, and distal to the deployed medical device.

16. The method of claim 13, wherein deploying the medical device is prior to delivering the minimally invasive device, wherein the delivering the minimally invasive device is proximal, within, or distal to the deployed medical device.

17. A method of treating a vessel wall, comprising:
i) deploying a stent;
ii) deploying a minimally invasive device, comprising:
   an introducer tube;
   a tubular member having a proximal end, a distal end, and a first lumen extending therebetween, the tubular member being slidably disposed within the introducer tube; and
   a plurality of hollow delivery struts disposed on the distal end of the tubular member and in fluid communication with the first lumen, each hollow delivery strut adapted to pierce through inner most layers of the vessel wall and each, comprising
      at least one exit port, and
      at least one stopper to prevent the delivery struts from piercing through the outer most layers of the vessel wall, the at last one stopper extending from the hollow delivery strut;
   an extension at a distal portion of at least one of the hollow delivery struts, the extension comprising at least one other exit port in fluid communication with the hollow delivery strut and;
iii) securing the hollow delivery struts at a treatment location in the vessel wall;
iv) administering the therapeutic or diagnostic agents through the hollow delivery struts into the vessel wall at the treatment location.

18. The method of claim 17, wherein deploying the stent is prior to delivering the minimally invasive device, wherein the delivering the minimally invasive device is proximal, within, and distal to the deployed stent.

19. The method of claim 17, wherein deploying the stent is following the treatment with the minimally invasive device.

* * * * *